(12) United States Patent
Malinin

(10) Patent No.: US 9,925,205 B2
(45) Date of Patent: Mar. 27, 2018

(54) COMPOSITIONS OF MULTICATIONIC DRUGS FOR REDUCING INTERACTIONS WITH POLYANIONIC BIOMOLECULES AND METHODS OF USE THEREOF

(71) Applicant: Insmed Incorporated, Monmouth Junction, NJ (US)

(72) Inventor: Vladimir Malinin, Plainsboro, NJ (US)

(73) Assignee: INSMED INCORPORATED, Bridgewater, NJ (US)

( * ) Notice: Subject to any disclaimer, the term of this patent is extended or adjusted under 35 U.S.C. 154(b) by 0 days.

(21) Appl. No.: 14/198,724

(22) Filed: Mar. 6, 2014

(65) Prior Publication Data

US 2014/0248335 A1 Sep. 4, 2014

Related U.S. Application Data

(63) Continuation of application No. 12/598,830, filed as application No. PCT/US2008/062469 on May 2, 2008, now abandoned.

(60) Provisional application No. 60/916,002, filed on May 4, 2007.

(51) Int. Cl.
A61K 31/7036 (2006.01)
A61K 9/127 (2006.01)
A61K 45/06 (2006.01)
A61K 9/50 (2006.01)

(52) U.S. Cl.
CPC .......... *A61K 31/7036* (2013.01); *A61K 9/127* (2013.01); *A61K 45/06* (2013.01); *A61K 9/5021* (2013.01)

(58) Field of Classification Search
CPC ............................ A61K 31/7036; A61K 9/127
See application file for complete search history.

(56) References Cited

U.S. PATENT DOCUMENTS

| | | | |
|---|---|---|---|
| 3,091,572 A | 5/1963 | Luedemann et al. |
| 3,136,704 A | 6/1964 | Charney |
| 4,235,871 A | 11/1980 | Paphadjopoulos et al. |
| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,515,736 A | 5/1985 | Deamer |
| 4,522,803 A | 6/1985 | Lenk et al. |
| 4,547,490 A | 10/1985 | Ecanow et al. |
| 4,588,578 A | 5/1986 | Fountain et al. |
| 4,606,939 A | 8/1986 | Frank et al. |
| 4,684,625 A | 8/1987 | Eppstein et al. |
| 4,693,999 A | 9/1987 | Axelsson et al. |
| 4,721,612 A | 1/1988 | Janoff et al. |
| 4,767,874 A | 8/1988 | Shima et al. |
| 4,833,134 A | 5/1989 | Kishimoto et al. |
| 4,857,311 A | 8/1989 | Domb et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,963,367 A | 10/1990 | Ecanow |
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,030,453 A | 7/1991 | Lenk et al. |
| 5,041,278 A | 8/1991 | Janoff et al. |
| 5,049,388 A | 9/1991 | Knight et al. |
| 5,049,389 A | 9/1991 | Radhakrishnan |
| 5,059,421 A | 10/1991 | Loughrey et al. |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Felgner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |

(Continued)

FOREIGN PATENT DOCUMENTS

| | | |
|---|---|---|
| CA | 2215716 C | 12/1999 |
| CA | 2614764 | 1/2007 |
| CA | 2838111 | 6/2007 |
| EP | 0069307 | 1/1983 |
| EP | 0274431 | 5/1994 |

(Continued)

OTHER PUBLICATIONS

Labiris, N. et al "Pulmonary drug delivery . . . " Br. J. Clin. Pharmacol. (2003) vol. 56, pp. 600-612.*
International Search Report and Written Opinion for International Application No. PCT/US2008/062469, dated Sep. 18, 2008.
International Preliminary Report on Patentability for International Application No. PCT/US2008/062469, dated Nov. 10, 2009.

(Continued)

*Primary Examiner* — Leigh C Maier
(74) *Attorney, Agent, or Firm* — Cooley LLP

(57) ABSTRACT

The present invention relates, in part, to a composition comprising a multicationic drug and an organic multianion. In some embodiments, the multicationic drug is enclosed within a carrier. In some embodiments, the carrier is a liposome. In some embodiments, the multicationic drug and organic multianion are enclosed within a carrier, while in other embodiments, the multicationic drug is enclosed within the carrier and the organic multianion is outside the carrier. The present invention also relates, in part, to a method of treating a subject for pulmonary distress comprising administering to a subject in need thereof the aforementioned composition.

20 Claims, 4 Drawing Sheets

(56) References Cited

U.S. PATENT DOCUMENTS

| | | |
|---|---|---|
| 5,409,704 A | 4/1995 | Bally et al. |
| 5,459,127 A | 10/1995 | Felgner et al. |
| 5,508,269 A | 4/1996 | Smith et al. |
| 5,540,936 A | 7/1996 | Coe et al. |
| 5,543,152 A | 8/1996 | Webb et al. |
| 5,569,464 A | 10/1996 | Endo et al. |
| 5,578,320 A | 11/1996 | Janoff et al. |
| 5,610,198 A | 3/1997 | Barry, III et al. |
| 5,614,216 A | 3/1997 | Janoff |
| 5,616,334 A | 4/1997 | Janoff et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Legace et al. |
| 5,665,383 A | 9/1997 | Grinstaff et al. |
| 5,723,147 A | 3/1998 | Kim et al. |
| 5,736,155 A | 4/1998 | Bally et al. |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,814,335 A | 9/1998 | Webb et al. |
| 5,820,848 A | 10/1998 | Boni et al. |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,922,350 A | 7/1999 | Janoff et al. |
| 5,945,122 A | 8/1999 | Abra et al. |
| 5,958,449 A | 9/1999 | Hersch et al. |
| 5,965,549 A | 10/1999 | Purwar et al. |
| 5,972,379 A | 10/1999 | Guo et al. |
| 5,993,850 A | 11/1999 | Sankaram et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,086,851 A | 7/2000 | Boni et al. |
| 6,090,407 A | 7/2000 | Knight et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,211,162 B1 | 4/2001 | Dale et al. |
| 6,221,388 B1 | 4/2001 | Hersch et al. |
| 6,228,393 B1 | 5/2001 | DiCosmo et al. |
| 6,274,175 B1 | 8/2001 | Gombotz et al. |
| 6,338,859 B1 | 1/2002 | Leroux et al. |
| 6,348,069 B1 | 2/2002 | Vacanti et al. |
| 6,352,996 B1 | 3/2002 | Cao et al. |
| 6,387,886 B1 | 5/2002 | Montgomery et al. |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,492,560 B2 | 12/2002 | Wilbur et al. |
| 6,497,901 B1 | 12/2002 | Royer |
| 6,509,323 B1 | 1/2003 | Davis et al. |
| 6,511,676 B1 | 1/2003 | Boulikas |
| 6,521,211 B1 | 2/2003 | Unger et al. |
| 6,521,736 B2 | 2/2003 | Watterson et al. |
| 6,596,305 B1 | 7/2003 | Edgerly-Plug |
| 6,599,912 B1 | 7/2003 | Au et al. |
| 6,613,352 B2 | 9/2003 | Lagace et al. |
| 6,615,824 B2 | 9/2003 | Power |
| 6,843,942 B2 | 1/2005 | Katinger et al. |
| 6,855,296 B1 | 2/2005 | Baker et al. |
| 6,900,184 B2 | 5/2005 | Cohen et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,991,809 B2 | 1/2006 | Anderson |
| 7,063,860 B2 | 6/2006 | Chancellor et al. |
| 7,100,600 B2 | 9/2006 | Loeffler et al. |
| 7,331,339 B2 | 2/2008 | Smith et al. |
| 7,368,102 B2 | 5/2008 | Tarara et al. |
| 7,544,369 B2 | 6/2009 | Boni et al. |
| 7,600,511 B2 | 10/2009 | Power et al. |
| 7,718,189 B2 | 5/2010 | Boni et al. |
| 7,748,377 B2 | 7/2010 | Smith et al. |
| 7,879,351 B2 | 2/2011 | Li et al. |
| 7,971,588 B2 | 7/2011 | Fink et al. |
| 8,100,162 B2 | 1/2012 | Joern et al. |
| 8,226,975 B2 | 7/2012 | Weers |
| 8,632,804 B2 | 1/2014 | Weers |
| 8,642,075 B2 | 2/2014 | Weers |
| 8,673,348 B2 | 3/2014 | Weers |
| 8,673,349 B2 | 3/2014 | Weers |
| 8,679,532 B2 | 3/2014 | Weers |
| 8,802,137 B2 | 8/2014 | Boni et al. |
| 9,114,081 B2 | 8/2015 | Gupta |
| 9,119,783 B2 | 9/2015 | Gupta |
| 9,333,214 B2 | 5/2016 | Gupta |
| 9,402,845 B2 | 8/2016 | Weers |
| 9,511,082 B2 | 12/2016 | Weers |
| 9,549,925 B2 | 1/2017 | Weers |
| 9,549,939 B2 | 1/2017 | Weers |
| 2001/0006660 A1 | 7/2001 | Legace et al. |
| 2002/0035061 A1 | 3/2002 | Krieger et al. |
| 2002/0052390 A1 | 5/2002 | Ponikau |
| 2002/0086852 A1 | 7/2002 | Cantor et al. |
| 2002/0187105 A1 | 12/2002 | Zou et al. |
| 2003/0059375 A1 | 3/2003 | Perez-Soler et al. |
| 2003/0096774 A1 | 5/2003 | Gonda et al. |
| 2003/0099697 A1 | 5/2003 | Panzner et al. |
| 2003/0118636 A1 | 6/2003 | Friesen et al. |
| 2003/0138481 A1 | 7/2003 | Zadi |
| 2003/0224039 A1 | 12/2003 | Boni et al. |
| 2004/0009126 A1 | 1/2004 | Pilkiewicz et al. |
| 2004/0032037 A1 | 2/2004 | Katinger et al. |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2004/0180082 A1 | 9/2004 | Kang et al. |
| 2005/0019926 A1 | 1/2005 | Gonda et al. |
| 2005/0025822 A1 | 2/2005 | Wong et al. |
| 2005/0042341 A1 | 2/2005 | Thomas et al. |
| 2005/0113337 A1 | 5/2005 | Taneja et al. |
| 2005/0214224 A1 | 9/2005 | Weers et al. |
| 2005/0217666 A1 | 10/2005 | Fink et al. |
| 2005/0220752 A1 | 10/2005 | Charmot et al. |
| 2005/0249795 A1 | 11/2005 | Zhang et al. |
| 2006/0062738 A1 | 3/2006 | Hofmann et al. |
| 2006/0067998 A1 | 3/2006 | Kurzrock et al. |
| 2006/0073198 A1 | 4/2006 | Boni et al. |
| 2006/0217603 A1 | 9/2006 | Nagai et al. |
| 2007/0077290 A1 | 4/2007 | Li et al. |
| 2007/0081963 A1 | 4/2007 | Oh et al. |
| 2007/0196461 A1 | 8/2007 | Weers |
| 2007/0267010 A1 | 11/2007 | Fink et al. |
| 2008/0089927 A1 | 4/2008 | Malinin |
| 2008/0131497 A1 | 6/2008 | Perkins et al. |
| 2008/0246472 A1 | 10/2008 | Igney et al. |
| 2009/0104256 A1 | 4/2009 | Gupta |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin et al. |
| 2010/0260829 A1 | 10/2010 | Boni et al. |
| 2011/0064796 A1 | 3/2011 | Cipolla et al. |
| 2011/0159079 A1 | 6/2011 | Li et al. |
| 2012/0010162 A1 | 1/2012 | Norling |

(56) References Cited

U.S. PATENT DOCUMENTS

| | | |
|---|---|---|
| 2012/0244206 A1 | 9/2012 | Cipolla et al. |
| 2013/0028960 A1 | 1/2013 | Weers |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0089598 A1 | 4/2013 | Gupta |
| 2013/0136788 A1 | 5/2013 | Gupta |
| 2013/0330400 A1 | 12/2013 | Perkins et al. |
| 2014/0072620 A1 | 3/2014 | Weers |
| 2014/0314835 A1 | 10/2014 | Boni et al. |
| 2015/0272880 A1 | 10/2015 | Seidel et al. |
| 2016/0113927 A1 | 4/2016 | Weers |
| 2016/0143849 A1 | 5/2016 | Gupta |
| 2016/0151402 A1 | 6/2016 | Gupta |
| 2016/0184301 A1 | 6/2016 | Weers |
| 2016/0184302 A1 | 6/2016 | Weers |
| 2016/0271125 A1 | 9/2016 | Boni et al. |
| 2016/0317563 A1 | 11/2016 | Weers |
| 2016/0317564 A1 | 11/2016 | Weers |
| 2016/0354371 A1 | 12/2016 | Weers |

FOREIGN PATENT DOCUMENTS

| | | |
|---|---|---|
| EP | 2457609 | 5/2012 |
| GB | 2145107 | 3/1985 |
| JP | 63-500175 | 1/1988 |
| JP | S63-239213 | 10/1988 |
| JP | 10-511363 | 11/1998 |
| JP | 2006-028069 | 2/2006 |
| UA | 27298 | 10/2007 |
| UA | 27804 | 11/2007 |
| WO | WO 85/00968 | 3/1985 |
| WO | WO 86/06959 | 12/1986 |
| WO | WO 87/00043 | 1/1987 |
| WO | WO 87/02219 | 4/1987 |
| WO | WO 88/04573 | 6/1988 |
| WO | WO 91/16882 | 11/1991 |
| WO | WO 93/12240 | 6/1993 |
| WO | WO 94/12155 | 6/1994 |
| WO | WO 94/12156 | 6/1994 |
| WO | WO 94/22430 | 10/1994 |
| WO | WO 96/08235 | 3/1996 |
| WO | WO 96/19199 | 6/1996 |
| WO | WO 96/19972 | 7/1996 |
| WO | WO 97/29851 | 8/1997 |
| WO | WO 99/30686 | 6/1999 |
| WO | WO 99/61003 | 12/1999 |
| WO | WO 99/65466 | 12/1999 |
| WO | WO 00/27359 | 5/2000 |
| WO | WO 00/29103 | 5/2000 |
| WO | WO 00/45791 | 8/2000 |
| WO | WO 01/05373 | 1/2001 |
| WO | WO 01/18280 | 3/2001 |
| WO | WO 01/32246 | 5/2001 |
| WO | WO 02/32400 | 4/2002 |
| WO | WO 02/43699 | 6/2002 |
| WO | WO 03/45965 | 6/2003 |
| WO | WO 03/075889 | 9/2003 |
| WO | WO 03/075890 | 9/2003 |
| WO | WO 04/002453 | 1/2004 |
| WO | WO 2004/047802 | 6/2004 |
| WO | WO 04/054499 | 7/2004 |
| WO | WO 04/110346 | 12/2004 |
| WO | WO 2006/108556 | 10/2006 |
| WO | WO 2007/011940 | 1/2007 |
| WO | WO 2007/012191 | 2/2007 |
| WO | WO 2007/067520 | 6/2007 |
| WO | WO 2007/117509 | 10/2007 |
| WO | WO 2007/117550 | 10/2007 |
| WO | WO 2008/039989 | 4/2008 |
| WO | WO 2008/137717 | 11/2008 |
| WO | WO 2008/137917 | 11/2008 |
| WO | WO 2010/045209 | 4/2010 |
| WO | WO 2013/177226 | 11/2013 |
| WO | WO 2015/017807 | 2/2015 |

OTHER PUBLICATIONS

International Search Report and Written Opinion for International Application No. PCT/US2006/027859, dated Aug. 14, 2007.
International Preliminary Report on Patentability for International Application No. PCT/US2006/027859, dated Jan. 22, 2008.
Office Action for U.S. Appl. No. 12/598,830, dated Mar. 7, 2012.
Office Action for U.S. Appl. No. 12/598,830, dated Oct. 23, 2012.
Allen, T. M. et al., "Effect of liposome size and drug release properties of pharmacokinetics of encapsulated drug to rats," The Journal of Pharmacology and Experimental Therapeutics, 226(2):539-544 (1983).
Alton et al., "Cationic lipid-mediated CFTR gene transfer to the lungs and nose of patients with cystic fibrosis: a double-blind placebo-controlled trial," The Lancet, 353(9157):947-954 (1999).
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against Pseudomonas aeruginosa in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in Klebsiella pneumoniae-infected lung tissue," The Journal Infectious Diseases, 171:938-947 (1995).
Ball, V. et al., "Complexation mechanism of bovine serum albumin and poly(allylamine hydrochloride)," J. Phys. Chem. B., 106(9):2357-2364 (2002).
Bangham, A. D. et al., "Diffusion of univalent ions across the lamellae of swollen phospholipids," J. Mol. Biol., 13:238-252 (1965).
Bangham, A. D., Introduction, "Liposomes: An Historical Perspective," in: Liposomes, Ostro, M. J. (ed.), pp. 1-25, Marcel Dekker, Inc., New York (1983).
Bargoni, A. et al., "Transmucosal transport of tobramycin incorporated in solid lipid nanoparticles (SLN) after duodenal administration to rats. Part I I—Tissue distribution," Pharmacological Research, 43(5):497-502 (2001).
Beaulac, C. et al., "Eradication of Mucoid Pseudomonas aeruginosa with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by Pseudomonas aeruginosa," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bermudez, L. E. et al., "Treatment of disseminated mycobacterium avium complex infection of beige mice with liposome-encapsulated aminoglycosides," The Journal of Infectious Diseases, 161(6):1262-1268 (1990).
Bunderberg de Jong, H. G. et al., Koazevation (Entmischung in Kolloidalen Systemen), Koll, Zeitsch, 50(10):39-48 (1930).
Carlier, M. B. et al., "Inhibition of lysosomal phospholipases by aminoglycoside antibiotics: in vitro comparative studies," Antimicrobial Agents and Chemotherapy, 23(3):440-449 (1983).
Chmiel, J. F. et al., "State of the art: why do the lungs of patients with cystic fibrosis become infected and why can't they clear the infection?", Respiratory Research, 4:8-20 (2003).
Costerton, J. W. et al., "Bacterial biofilms: A common cause of persistent infections," Science, 284:1318-1322 (1999).

(56) References Cited

OTHER PUBLICATIONS

Couvreur, P. et al., "Liposomes and nanoparticles in the treatment of intracellular bacterial infections," Pharmaceutical Research, 8(9):1079-1085 (1991).
Cynamon, M. H. et al., "Liposome-Encapsulated-Amikacin Therapy of Mycobacterium avium Complex Infection in Geige Mice," Antimicrobial Agents and Chemotherapy, 33(8):1179-1183 (1989).
Dally, M. B. et al., "Ventilatory effects of aerosol gentamicin," Thorax, 33:54-56 (1978).
Damaso, D. et al., "Susceptibility of current clinical isolates of Pseudomonas aeruginosa and enteric gram-negative bacilli to amikacin and other aminoglycoside antibiotics," The Journal of Infectious Diseases, 134:S394-S390 (1976).
Deamer, D. W. et al., "Liposome Preparation: Methods and Mechanisms," Chapter 1 in: Liposomes, Ostro, M. J. (ed.), Marcel Dekker, Inc., New York (1983), 27 pages.
Demaeyer, P. et al., "Disposition of liposomal gentamicin following intrabronchial administration in rabbits," Journal Microencapsulation, 10(1):77-88 (1993).
Deol, P. et al., "Lung specific stealth liposomes: stability, biodistribution and toxicity of liposomal antitubular drugs in mice," Biochemica et Biophysica Acta, 1334:161-172 (1997).
Dickie, K. J. et al., "Ventilatory effects of aerosolized kanamycin and polymyxin," Chest, 63(5):694-697 (1973).
Doring, G. et al., "Antibiotic therapy against Pseudomonas aeruginosa in cystic fibrosis: a European consensus," Eur Respir J., 16(4):749-767 (2000).
Drenkard, E. et al., "Pseudomonas biofilm formation and antibiotic resistance are linked to phenotypic variation," Nature, 416:740-743 (2002).
Ehlers, S. et al., "Liposomal amikacin for treatment of M. avium Infections in clinically relevant experimental settings," Zbl. Bakt., 284:218-231 (1996).
Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).
Finke, W., "Long-term antibiotic therapy in chronic bronchitis and infectious asthma. Control and prevention of bronchopulmonary disease." Antibiotics and Chemotherapy, 4(3):319-329 (1954).
Fountain, M. W. et al., "Treatment of *Brucella canis* and *Brucella abortus* In vitro and in vivo by stable plurilamellar vesicle-encapsulated aminoolycosides," The Journal of Infectious Diseases, 152(3):529-535 (1985).
Garcia, A. T., "Efficacy of amikacin sulfate in lower respiratory infections," Investigacion Medica Internacional, 9(3):235-240 (1982) (with English Abstract).
Geller, D. E. et al., "Pharmacokinetics and bioavailability of aerosolized tobramycin in cystic fibrosis," Chest, 122(1):219-226 (2002).
Gibson, R. L. et al., "Pathophysiology and management of pulmonary infections in cystic fibrosis," American Journal of Respiratory and Critical Care Medicine, 168(8):918-951 (2003).
Gibson, R. L. et al., "Significant microbiological effect of inhaled tobramycin in young children with cystic fibrosis," American Journal of Respiratory and Critical Care Medicine, 167(6):841-849 (2003).
Gonzales-Rothi, R. J. et al., "Liposomes and pulmonary alveolar macrophages: functional and morphologic interactions," Experimental Lung Research, 17:687-705 (1991).
Hoffman, L. R. et al., "Aminoglycoside antibiotics induce bacterial biofilm formation," Nature, 436:1171-1175 (2005).
Hrkach, J. S. et al., "Synthesis of poly(L-lactic acid-co-L-lysine) graft copolymers," Macromolecules, 28:4736-4739 (1995).
Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (eds.), American Chemical Society, pp. 93-102 (1996).

Hunt, B. E. et al., "Macromolecular mechanisms of sputum inhibition of tobramycin activity," Antimicrobial Agents and Chemotherapy, 39(1):34-39 (1995).
Ishii, F. et al., "Procedure for Preparation of Lipid Vesicles (Liposomes) Using the Coacervation (Phase Separation) Technique," Langmuir, 11(2):483-486 (1995).
Janoff, A. S. et al., "Unusual lipid structures selectively reduce the toxicity of amphotericin B," Proc. Nat. Acad. Sci, USA, 85:6122-6126 (1988).
Johansson, J., "Structure and properties of surfactant protein C," Biochimica et Biophysica Acta, 1408:161-172 (1998).
Katare, O. P. et al., "Enhanced in vivo Performance of LiposomalIndomethacin Derived From Effervescent Granule Based Proliposomes," J. Microencapsulation, 12(5):487-493 (1995).
Kesavalu, L. et al., "Differential effects of free and liposome encapsulated amikacin on the survival of *Mycobacterium avium* complex in mouse peritoneal macrophages," Tubercle, 71:215-218 (1990).
Kim, E. K. et al., "Pharmacokinetics of intravitreally injected liposomes encapsulated tobramycin in normal rabbits," Yonsei Medical Journal, 31(4):308-314 (1990).
Klemens, S. P. et al., "Liposome-encapsulated-gentamicin therapy of *Mycobacterium avium* complex infection in beige mice," Antimicrobial Agents and Chemotherapy, 34(6):967-970 (1990).
Lagace, J. et al., "Liposome-encapsulated antibiotics: preparation, drug release and antimicrobial activity against Pseudomona aeruginosa," Journal Microencapsulation, 8(1) 53-61 (1991).
Le Brun, P. P. H. et al., "A review of the technical aspects of drug nebulization," Pharmacy World & Science, 22(3):75-81 (2000).
Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).
Le Brun, P. P. H. et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Marier, J. F. et al., "Liposomal tobramycin against pulmonary infections of Pseudomonas aeruginosa: a pharmacokinetic and efficacy study following single and multiple intratracheal administrations in rats," Journal Antimicrobial Chemotherapy, 52:247-252 (2003).
Marier, J-F. et al., "Pharmacokinetics and efficacies of liposomal and conventional formulations of tobramycin after intratracheal administration in rats with pulmonary burkholderia cepacia infection," Antimicrobial Agents and Chemotherapy, 46(12):3776-3781 (2002).
Meers, P. et al., "Biofilm penetration, triggered release and in vivo activity of inhaled liposomal amikacin in chronic Pseudomonas aeruginosa lung infections," J. Antimicrob, Chemother., 61(4):859-868 (2008).
Mendelman, P. M. et al., "Aminoglycoside penetration, inactivation, and efficacy in cystic fibrosis sputum," American Review of Respiratory Disease, 132(4):761-765 (1985).
Mohanty, B. et al., "Systematic of alcohol-induced simple coacervation in aqueous gelatin solutions," Biomacromolecules, 4:1080-1086 (2003).
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium* intracellulare complex bacteremia in AIDS patients," Antimicrobial Agents and Chemotherapy, 37(9):1869-1872 (1993).
Niven, R. W. et al., "Nebulization of liposomes. I. Effects of lipid composition,"Pharmaceutical Research, 7(11):1127-1133 (1990).

(56) References Cited

OTHER PUBLICATIONS

Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of the Mayo Clinic and The Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953 (1947).
Omri, A. et al., "Incorporation, release and in-vitro antibacterial activity of liposomal aminoglycosides against Pseudomonas aeruginosa," Journal Antimicrobial Chemotherapy, 36(4):631-639 (1995).
Omri, A. et al., "Comparison of the bactericidal action of amikacin, netilmicin and tobramtcin in free and liposomal formulation against pseudomonas aeruginosa," Chemotherapy, 42:170-176 (1996).
Omri, A. et al., "Pulmonary retention of free and liposome-encapsulated tobramycin after intratracheal administration in uninfected rats and rats infected with Pseudomonas aeruginosa," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Papahadjopoulos, D. et al., "Phospholipid model membrames. I. Structrual characteristics of hydrated liquid crystals," Biochimica et Biophysica Acta., 135:624-638 (1967).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).
Patton, J. S. et al., "The lungs as a portal of entry for systemic drug delivery, " Proc. Am. Thor. Soc., 1:338-344 (2004).
Petersen, E. A. et al., "Liposomal amikacin: improved treatment of Mycibacterium avium complex infection in the beige mouse model," Journal Antimicrobial Chemotherapy, 38:819-828 (1996).
Pilewski, J. M. et al., "Role of CFTR in airway disease," Physiological Reviews, 79(1):S215-S255 (1999).
Pines, A. et al., "Treatment of severe pseudomonas infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Aerosol Antibiotic Therapy, 25:436-448 (1949).
Poyner, E. A. et al., "Preparation, properties and the effects of free and liposomal tobramycin on siderophore production by Pseudomonas aeruginosa," Journal of Antimicrobial Chemotherapy, 34:43-52 (1993).
Price, C. I. et al., "Liposome delivery of aminoglycosides in burn wounds," Surgery, Gynecolooy & Obstetrics, 174:414-418 (1992).
Sabra, W. et al., "Physiological responses of pseudomonas aeruginosa PAO1 to oxidative stress in controlled microaerobic and aerobic cultures," Microbiology, 148:3195-3202 (2002).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).
Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).
Stott, P. W. et al., "Characterization of complex coacervates of some tricyclic antidepressants and evaluation of their potential for enhancing transdermal flux," Journal of Controlled Release, 41(3):215-227 (1996).
Shah, S. P. et al., "Liposomal amikacin dry powder inhaler: effect of fines on in vitro performance," AAPS PharmSciTech, 5(4):e65:1-7 (2004).
Smith, A. L. et al., "Safety of aerosol tobramycin administration for 3 months to patients with cystic fibrosis," Pediatric Pulmonology, 7:265-271 (1989).
Swenson, K. A. et al., "Pharmacokinetics and in vivo activity of liposome-encapsulated gentamicin," Antimicrobial Agents and Chemotherapy, 34(2)235-240 (1990).
Swenson, C. E. et al., "Liposomal aminoglycosides and TLC G-65," Aids Patient Care, pp. 290-296 (1991).
Szoka, F. Jr. et al., "Comparative properties and methods of preparation of lipid vesicles (liposomes)," Ann. Rev. Biophys, Bioeng., 9:467-508 (1980).
Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of Pseudomonas aeruginosa to collagen type I," Antimicrobial Agents and Chemotherapy, 39(12):2645-2649 (1995).
Veldhuizen, R. et al., "The role of lipids in pulmonary surfactant," Biochimica et Biophysica Acta, 1408:90-108 (1998).
Vidgren, M. et al., "A study of $^{99m}$ technetium-labelled beclomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Wang, W. et al., "Research progress in pulmonary administration of liposome," Journal of Shenyang Pharmaceutical University, 17(3)226-229 (2000).
Westerman, E. M. et al., "Effect of nebulized colistin sulphate and colistin sulphomethate on lung function in patients with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Wichert, B. V. et al., "Amikacin liposomes: characterization, aerosolization, and in vitro activity against *Mycobacterium avium*—intracellulare in alveolar macrophages," International Journal of Pharmaceutics, 78(2-3)227-235 (1992).
Wolff, R. K. et al., "Toxicologic testing of inhaled pharmaceutical aerosols," Critical Reviews in Toxicology, 23(4):343-369 (1993).
Worlitzsch, D. et al., "Effects of reduced mucus oxygen concentration in airway pseudomonas infections of cystic fibrosis patients," J. Clin. Invest., 109:317-325 (2002).
Xiu, L. et al., "Drug Resistant Analysis of Pseudomonas Aeruginosa in Patients with Mechanical Ventilation," Med. J. Chin. PLA, 27(6):544-545 (2002) (Abstract).
Yanagihara, K. et al., "Design of anti-bacterial drug and anti-Mycobacterial drug for drug delivery system," Current Pharmaceutical Design, 8:475-482 (2002).
Zeng, S. et al., "Intravitreal Pharmacokinetics of Liposome-encapsulated Amikacin in a Rabbit Model," Opthamology, 100:1640-1644 (1993).
Zhang, J. H. et al., "A Novel Method to Prepare Liposomes Containing Amikacin," Journal Microencapsulation, 16(4):511-516 (1999).
Zlatanov, Zl, et al., "Gentamycin-pharmachim. Aerosol inhalation treatment of patients with chronic bronchitis," Medico Biologic Information 2, pp. 5-8 (1976).

(56) References Cited

OTHER PUBLICATIONS

International Search Report and Written Opinion for International Application No. PCT/US2008/062868, dated Sep. 18, 2008, 7 pages.
International Preliminary Report on Patentability for International Application No. PCT/US2008/062868, dated Nov. 10, 2009, 5 pages.
Supplementary European Search Report for European Application No. 09821103.0, dated Aug. 12, 2015, 10 pages.
Written Opinion for International Application No. PCT/US2009/060468, dated Jun. 24, 2010, 3 pages.
International Preliminary Report on Patentability for International Application No. PCT/US2009/060468, dated Apr. 19, 2011, 4 pages.
Supplementary European Search Report for European Application No. 03816990.0, dated Jan. 12, 2009, 5 pages.
International Search Report for International Application No. PCT/US2003/034240, dated Jul. 12, 2005, 1 page.
International Preliminary Report on Patentability for International Application No. PCT/US2003/034240, dated May 6, 2013, 5 pages.
Supplementary European Search Report for European Application No. 06787716.7, dated Dec. 29, 2011, 7 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
Supplementary European Search Report for European Application No. 07754853, dated Jan. 16, 2013, 8 pages.
International Search Report and Written Opinion for International Application No. PCT/US2007/008404, dated Sep. 26, 2008, 6 pages.
International Preliminary Report on Patentability for International Application No. PCT/US2007/008404, dated Oct. 21, 2008, 4 pages.
European Search Report for European Patent Application No. 11159754.8, dated Jun. 22, 2011, 5 pages.
European Search Report for European Patent Application No. 13175824.5, dated Sep. 16, 2013, 8 pages.
European Search Report for European Application No. 14183066.1, dated Dec. 16, 2014, 11 pages.
Supplementary European Search Report for European Application No. 06847502.9, dated Dec. 5, 2012, 7 pages.
International Search Report and Written Opinion for International Application No. PCT/US2006/046360, dated Oct. 17, 2007, 5 pages.
International Preliminary Report on Patentability for International Application No. PCT/US2006/046360, dated Jun. 11, 2008, 5 pages.
European Search Report for European Application No. 16156100.6, dated Jul. 25, 2016, 6 pages.
European Search Report for European Application No. 16156099.0, dated Jul. 25, 2016, 7 pages.
Supplementary European Search Report and Written Opinion for European Application No. 07754936.8, dated Jan. 18, 2013, 9 pages.
International Search Report and Written Opinion for International Application No. PCT/US2007/008500, dated Sep. 26, 2008, 9 pages.
International Preliminary Report on Patentability for International Application No. PCT/US2007/008500, dated Oct. 21, 2008, 8 pages.
Supplementary European Search Report for European Application No. 13793204.2, dated Sep. 25, 2015, 5 pages.
International Search Report and Written Opinion for International Application No. PCT/US2013/042113, dated Sep. 4, 2013, 13 pages.
International Preliminary Report on Patentability for International Application No. PCT/US2013/042113, dated Nov. 25, 2014, 9 pages.

Bakker-Woudenberg, I. A. J. M. et al., "Long-Circulating Sterically Stabilized Liposomes in the Treatment of Infections," Method in Enzymology, Available online Feb. 21, 2005, 391:228-260 (2005).
Bakker-Woudenberg et al. (2002). Ciprofloxacin in polyethylene glycol-coated liposomes: efficacy in rat models of acute or chronic Pseudomonas aeruginosa infection. Antimicrobial Agents and Chemotherapy 46(8), pp. 2575-2581.
Bakker-Woudenberg et al. (2001). Improved efficacy of ciprofloxacin administered in polyethylene glycol-coated liposomes for treatment of Klebsiella pneumoniae pneumonia in rats. Antimicrobial Agents and Chemotherapy 45(5), pp. 1487-1492.
Bedard et al. (1989). Interaction of the fluoroquinolone antimicrobial agents ciprofloxacin and enoxacin with liposomes. Antimicrobial Agents and Chemotherapy 33(8), pp. 1379-1382.
Bhavane, R. et al., "Agglomerated vesicle technology: a new class of particles for controlled and modulated pulmonary drug delivery," Journal of Controlled Release 93(1):15-28 (Nov. 2003).
Bhavane (2006). Nanoparticle agglomerates for pulmonary drug delivery. A dissertation presented to the faculty of the University of Texas Health Science Center at Houston of Health Information Sciences. UMI No. 3237380.
Bilodeau, M. et al., "Kanamycin aerosol therapy in 200 cases of bronchopulmonary suppurations," Can. Med. Assoc. J., 89:537-541 (1963) (with English Abstract).
Blaser, J. et al., "Once daily dosing of aminoglycosides," Eur. Clin. Microbiol. Infect. Dis., 14(12):1029-1038 (1995).
Bucke, W. E. et al., "Surface-modified amikacin-liposomes: organ distribution and interaction with plasma proteins," Journal of Drug Targeting, 5(2):99-108 (1997).
Cantin, A. M. et al., "Aerosolized prolastin suppresses bacterial proliferation in a model of chronic pseudomonas aeruginosa lung infection," Am. J. Respir. Crit. Care Med., 160:1130-1135 (1999).
Cash, H. A. et al., "A rat model of chronic respiratory infection with Pseudomonas aeruginosa," American Review of Respiratory Disease, 119(3):453-459 (1979).
Challoner, P. B. et al., "Gamma Scintigraphy Lung Deposition Comparison of TOBI in the PARI LC PLUS Nebulizer and the Aerodose Inhaler," American Thoracic Society 97th International Conference, San Francisco, California, Aerogen, Inc. (2001).
Chambless, J. D. et al., "A three-dimensional computer model of four hypothetical mechanisms protecting biofilms from antimicrobials," Appl. Environ. Microbiol., 72(3):2005-2013 (2006).
Chan, C. H. S. et al., "Mycobacteria as a cause of infective exacerbation in bronchiectasis," Postgrad. Med. J., 68:896-899 (1992).
Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).
Ciofu, O. et al., "Occurrence of Hypermutable Pseudomonas aeruginosa in Cystic Fibrosis Patients Is Associated with the Oxidative Stress Caused by Chronic Lung Inflammation," Antimicrobial Agents and Chemotherapy, 49(6):2276-2282 (Jun. 2005).
Clancy, J. P. et al., "Phase II studies of nebulised Arikace in CF patients with Pseudomonas aeruginosa infection," Thorax, 68(9):818-825 (2013).
Clay. M. M. et al., "Assessment of jet nebulisers for lung aerosol therapy," Lancet, 2:592-594 (1983).
ClinicalTrials.gov, "Safety and Efficacy Study of Ciprofloxacin for Inhalation in Patients With Non-Cystic Fibrosis Bronchiectasis 'ORBIT-1'", Identifier: NCT00889967, First Received: Apr. 27, 2009, 3 pages.
Colardyn, F., "The efficacy and safety of isepamicin and ceftazidime compared with amikacin and ceftazidime in acute lower respiratory tract infection," Journal of Chemotherapy, 7(2):129-135 (1995).
Coleman, L. T. et al., "Bronchiectasis in children," Journal of Thoracic Imaging, 10(4)268-279 (1995).
Comis, R. L., "Carboplatin in the treatment of non-small cell lung cancer: a review," Oncology, 50(2):37-41 (1993).
Conley et al., "Aerosol Delivery of Liposome-Encapsulated Ciprofloxacin: Aerosol Characterization and Efficacy against Francisella tularensis Infection in Mice," Antimicrobial Angents, 41(6):1288-1292 (Jun. 1997).

(56) References Cited

OTHER PUBLICATIONS

Cooksey, R. C. et al., "Antimicrobial susceptibility patterns of *Streptococcus pneumoniae*," Antimicrobial Agents and Chemotherapy, 13(4):645-648 (1978).
Cremades, M. J. et al., "Repeated pulmonary infection by Nocardia asteroides complex in a patient with bronchiectasis," Respiration, 65:211-213 (1998).
Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998).
Currie, D. C., "Nebulisers for bronchiectasis," Thorax, 52(Suppl. 2):S72-S74 (1997).
Cymbala, A. A. et al., "The Disease-Modifying Effects of Twice-Weekly Oral Azithromycin in Patients with Bronchiectasis," Treat Respir. Med. 2005;4(2):117-122.
Dees, C. et al., "The mechanism of enhanced intraphagocytic killing of bacteria by liposomes containing antibiotics," Veterinary Immunology and Immunopathology, 24:135-146 (1990).
Del Porto, P. et al., "Dysfunctional CFTR alters the bactericidal activity of human macrophages against Pseudomonas aeruginosa," PLoS One, 6(5):e19970 (2011).
Dequin, P. F. et al., "Urinary excretion reflects lung deposition of aminoglycoside aerosols in cystic fibrosis," Eur. Respir. J., 18(2):316-322 (2001).
Desai et al., "A facile method of delivery of liposomes by nebulization," Journal of Controlled Release, 84(1-2):69-78 (2002).
Desai, T. R. et al., "Determination of surface free energy of interactive dry powder liposome formulations using capillary penetration technique," Colloids and Surfaces B: Biointerfaces, 22:107-113 (2001).
Desai, "Delivery of liposomes in dry powder form: aerodynamic dispersion properties," European Journal of Pharmaceutical Sciences 20:459-467 (2003).
Di Ninno et al. (1993). Liposome-encapsulated ciprofloxacin is effective in the protection and treatment of BALB/c mice against Francisella tularensis. The Journal of Infectious Diseases 168, pp. 793-794.
Dong, C. et al., "Acacia-gelatin microencapsulated liposomes: preparation, stability and release of acetylsalicylic acid," Pharmaceutical Research, 10(1):141-146 (1993).
Eboka (2005). Aqueous solubility of ciprofloxacin in the presence of metal cations. Tropical Journal of Pharmaceutical Research, 4(1), pp. 349-354.
Eigen (1995). A multicenter study of alternate-day prednisone therapy in patients with cystic fibrosis. The Journal of Pediatrics, 126(4), pp. 515-523.
El-Din, M. A. T. et al., "Nebulizer therapy with antibiotics in chronic suppurative lung disease," Journal of Aerosol Medicine, 7(4):345-350 (1994).
Farber, J. E. et al., "The use of aerosol penicillin and streptomycin in bronchopulmonary infections," California Medicine, 73(3):214-217 (1950).
Finlay, W. H. et al., "Regional lung deposition of nebulized liposome-encapsulated ciprofloxacin," International Journal of Pharmaceutics (Amsterdam), 167(1-2):121-127 (Jun. 1, 1998).
Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).
Gleiser, C. A. et al., "Pathology of experimental respiratory anthrax in Macaca mulatta," Brit. J. Exp. Path., 44:416-426 (1963).
Goldman, J. M. et al., "Inhaled micronised gentamicin powder: a new delivery system," Thorax, 45:939-940 (1990).
Goss, C. H. et al., "Update on cystic fibrosis epidemiology," Current Opinion in Pulmonary Medicine, 10(6):510-514 (2004).
Graczyk, J. et al., "*Staphylococcal* pneumonia—analysis of material of patients treated in lung diseases hospital in years 1981-1994," Pneumonologia I Alergologia Polska, 65(11-12):767-774 (1997) (with English Abstract).
Greene, K. E. et al., "Radiographic changes in acute exacerbations of cystic fibrosis in adults: A pilot study," AJR, 163:557-562 (1994).
Gunther, A. et al., "Surfactant alteration and replacement in acute respiratory distress syndrome," Respiratory Research, 2(6): 353-364 (2001).
Gursoy et al. (1997). Characterization of ciprofloxacin liposomes; derivative ultraviolet spectrophotometric determinations. J. Microencapsulation 14(6), pp. 769-776.
Hagwood, S. et al., "Structure and properties of surfactant protein B," Biochimica et Biophysica Acta., 1408:150-160 (1998).
Hansen, C. R. et al., "Long-term azithromycin treatment of cystic fibrosis patients with chronic pseudomonas aeruginosa infection: an observational cohort study," Journal of Cystic Fibrosis, 4(1):35-40 (2005).
Helbich, T. et al., "High-resolution computed tomography of the lung in young patients with cystic fibrosis," Radiologe, 33(3):142-146 (1993) (English Abstract).
Hess, D. et al., "Medication nebulizer performance. Effects of diluent volume, nebulizer flow, and nebulizer brand," Chest, 110:498-505 (1996).
Hess, D. R., "Nebulizers: Principles and Performance," Respiratory Care, 45(6):609-622 (2000).
Hewitt, W. L. et al., "Antibiotic therapy of abscess of the lung and bronchiectasis," California Medicine, 76(5):319-324 (1952).
Honeybourne, D., "Antibiotic penetration in the respiratory tract and implications for the selection of antimicrobial therapy," Current Opinion in Pulmonary Medicine 1997, 3(2):170-174.
Howell, S. B., "Clinical applications of a novel sustained-release injectable drug delivery system: Depofoam Technology," Cancer Journal, 7:219-227 (2001).
Huang et al. (2006). Pulmonary delivery of insulin by liposomal carriers. Journal of Controlled Release 113, pp. 9-14.
Hubble, D., "Discussion on respiratory catarrh in children," Proceedings of the Royal Society of Medicine, 52(9):701-710 (1959).
Hung, O. R. et al., "Pharmacokinetics of inhaled liposome-encapsulated fentanyl," Anesthesiology, 83(2): 277-284 (Aug. 1995).
Hung, J. C. et al., "Evaluation of two commercial jet nebulisers and three compressors for the nebulisation of antibiotics," Archives of Disease in Childhood, 71(4):335-338 (Oct. 1994).
Ikegami, M. et al., "Surfactant protein metabolism in vivo," Biochimica et Biophysica Acta, 1408:218-225 (1998).
Ikemoto, H. et al., "Susceptibility of bacteria isolated from the patients with lower respiratory tract infections to antibiotics," The Japanese Journal of Antibiotics, 42(11):2350-2353 (1989).
Ip, M. S. M. et al., "Bronchiectasis and related disorders," Respirology, 1:107-114 (1996).
Jayaraman, S. et al., "Noninvasive in vivo fluorescence measurement of airway-surface liquid depth, salt concentration, and pH," J. Clin. Invest. 107:317-324 (2001).
Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Knoch, M. et al., "The customised electronic nebuliser: a new category of liquid aerosol drug delivery systems," Expert Opin. Drug Deliv., 2(2):377-390 (2005).
Knox, K. et al., "Chronic bronchitis. An attempt to control chronic infection with Haemophilus influenzae by aerosol therapy," The Lancet, pp. 120-122 (1955).
Landyshev, Y. S. et al., "Clinical and experimental aspects of liposomal hydrocortisone treatment of bronchial asthma," Ter. Arkh., 74(8):45-48 (2002).
Lass, J. S. et al., "New advances in aerosolised drug delivery: vibrating membrane nebuliser technology," Expert Opin Drug Deliv., 3(5):693-702 (2006).
Li, Z. et al., "Nebulization of liposomal amikacin formulations: SLIT Amikacin," Respiratory Drug Delivery, 3:801-804 (2006).

(56) References Cited

OTHER PUBLICATIONS

Li, Z. et al., "Characterization of nebulized liposomal amikacin (Arikace) as a function of droplet size," Journal of Aerosol Medicine and Pulmonary Drug Delivery, 21(3):245-253 (2008).
Lin, H.-C. et al., "Inhaled gentamicin reduces airway neutrophil activity and mucus secretion in bronchiectasis," Am. J. Respir. Crit. Care Med., 155:2024-2029 (1997).
Magallanes, M. et al., "Liposome-incorporated ciprofloxacin in treatment of murine salmonellosis," Antimicrobial Agents and Chemotherapy, Nov. 1993, 37(11):2293-2297.
Majumdar, S. et al., "Efficacies of Liposome-Encapsulated Streptomycin and Ciprofloxacin against Mycobacterium avium-M. intracellulare Complex Infections in Human Peripheral Blood Monocyte/Macrophages," Antimicrobial Agents and Chemotherapy, 36(12):2808-2815 (Dec. 1992).
Marcotte, G. V. et al., "Chronic productive cough and bronchiectasis in a 40-year-old woman," Annals of Allergy, Asthma & Immunology, 78(6):559-564 (1997).
Mariotti, A. B. et al., "Aerosol therapy with tobramycin in exacerbations of chronic obstructive lung disease (7 cases)," 66(2):198-202 (1996) (with English Abstract).
Martini, W. Z. et al., "Lung surfactant kinetics in conscious pigs," Am J Physiol., 277(1 Pt 1): E187-E195 (1999).
Marwah, O. S. et al., "Bronchiectasis. How to identify, treat and prevent," Postgrad. Med., 97(2):149-150, 153-156, 159 (1995) (Abstract).
Maurer, N. et al., "Anomalous solubility behavior of the antibiotic ciprofloxacin encapsulated in liposomes: a $^1$H-NMR study," Biochimica et Biophysica Acta, 1374:9-20 (1998).
McAllister, S. M. et al., "Antimicrobial properties of liposomal polymyxin B," Journal of Antimicrobial Chemotherapy, 43:203-210 (1999).
Mercer, R. R. et al., "Cell Number and Distribution in Human and Rat Airways," Am. J. Respir. Cell Mol. Biol., vol. 10, pp. 613-624, 1994.
Mombelli, G. et al., "Anti-pseudomonas activity in bronchial secretions of patients receiving amikacin or tobramycin as a continuous infusion," Antimicrobial Agents and Chemotherapy, 19(1):72-75 (1981).
Montero et al. (1998). Fluoroquinolone-biomembrane interactions: monolayer and calorimetric studies. Langmuir 14(9), pp. 2451-2454.
Morgan, J. R. et al., "Preparation and properties of liposome-associated gentamicin," Antimicrobial Agents and Chemotherapy, 17(4):544-548 (1980).
Myers, M. A. et al., "Pulmonary effects of chronic exposure to liposome aerosols in mice," Experimental Lung Research, 19:1-19 (1993).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
Oh, Y-K et al., "Formulation and Efficacy of Liposome-Encapsulated Antibiotics for Therapy of Intracellular *Mycobacterium avium* Infection," Antimicrobial Agents and Chemotherapy, 39(9):2104-2111 (Sep. 1995).
Perkins, W. R. et al., "Aerosolization of liposomal amikacin (Arikace) using different nebulizers: Selection of the eflow nebulizer," Poster and Oral Presentation at North American Cystic Fibrosis Conference (Oct. 2007), Pediatric Pulmonology, 42(30):356-357, abs. 434, 12 pages.
Perkins, W. R. et al., "Role of lipid polymorphism in pulmonary surfactant," Science, 273:330-332 (Jul. 1996).
Petkowicz, J. et al., "Hypoglycemic Effect of Liposome-Entrapped Insulin Administered by Various Routes into Normal Rats," Pol. J. Pharmacol. Pharm., 41:299-304 (1989).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).

Press Release, "Transave Announces Positive Phase II Results for Once-Daily Arikace in the Treatment of Cystic Fibrosis Patients Who Have Pseudomonas Lung Infections," Presented at the European Cystic Fibrosis Society Conference, Monmouth Junction, NJ, Jun. 13, 2008, 3 pages.
Price, C. I. et al., "Liposome encapsulation: a method for enhancing the effectiveness of local antibiotics," Surgery, 115(4):480-487 (1994).
Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O–C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Rastogi et al. (2006). Particulate and vesicular drug carriers in the management of tuberculosis. Current Drug Delivery 3(1), pp. 121-128.
Rau, J. L. et al., "Performance Comparison of Nebulizer Designs: Constant-Output, Breath-Enhanced, and Dosimetric," Respir. Care 2004;49(2):174-179.
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Schaad, U. B. et al., "Efficacy of inhaled amikacin as adjunct to intravenous combination therapy (ceftazidime and amikacin) in cystic fibrosis," Journal of Pediatrics, 111(4):599-605 (Oct. 1987).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. et al., "Liposome-encapsulated aminoglycosides in pre-clinical and clinical studies," Journal of Antimicrobial Chemotherapy, 48:333-344 (2001).
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Sermet-Gaudelus, I. et al., "Nebulized antibiotics in cystic fibrosis," Pediatric Drugs, 4(7):455-467 (2002).
Shima, K. et al., "A study of amikacin (BB-K8) on the clinical effects on the respiratory infection," Chemotherapy, 23(6):2128-2130 (1975) (with English Abstract).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Smith et al. (1986). Pharmacokinetics and sputum penetration of ciprofloxacin in patients with cystic fibrosis. Antimicrobial Agents and Chemotherapy 30(4), pp. 614-616.
Sweeney et al. (2005). Spray-freeze-dried liposomal ciprofloxacin powder for inhaled aerosol drug delivery. International Journal of Pharmaceutics 305, pp. 180-185.
Tarran, R., "Regulation of Airway Surface Liquid Volume and Mucus Transport by Active Ion Transport," Proc. Am. Thorac. Soc., vol. 1, pp. 42-46, 2004.
Takamoto, M. et al., "Imipenem/cilastatin sodium alone or combined with amikacin sulfate in respiratory infections," The Japanese Journal of Antibiotics, 47(9):1131-1144 (1994) (with English Abstract).

(56) References Cited

OTHER PUBLICATIONS

Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).

Taylor, K. M. G. et al., "The influence of liposomal encapsulation on sodium cromoglycate pharmacokinetics in man," Pharmaceutical Research, 6(7):633-636 (1989).

Ten, R. M. et al., "Interleukin-2 liposomes for primary immune deficiency using the aerosol route," International Immunopharmacology, 2(2-3):333-344 (2002).

Terzano, C. et al., "Tobramycin aerosol: could the delivery system influence the particle size and deposition in the lower airways?" Recenti. Prog. Med., 89(5):245-249 (1998) (English Abstract).

Thomas, D. A. et al., "Acute effects of liposome aerosol inhalation on pulmonary function in healthy human volunteers," Chest, 99(5):1268-1270 (1991).

Ulrich, A. S., "Biophysical aspects of using liposomes as delivery vehicles," Bioscience Reports, 22(2):129-150 (Apr. 2002).

Van Der Straeten, M. et al., "Amikacin in the treatment of gram-negative bronchopulmonary infections," The Journal of Infectious Diseases, 134:S391-S393 (1976).

Vecellio, L., "The mesh nebuliser: a recent technical innovation for aerosol delivery," Breathe, 2(3):253-260 (2006).

Webb, M. S. et al., "Antibacterial Efficacy against an In Vivo *Salmonella typhimurium* Infection Model and Pharmacokinetics of a Liposomal Ciprofloxacin Formulation," Antimicrobial Agents and Chemotherapy, 42(1):45-52 (Jan. 1998).

Weber et al. (1997). Effect of nebulizer type and antibiotic concentration on device performance. Pediatric Pulmonology 23, pp. 249-260.

Wise et al. (1983). In vitro activity of Bay 09867, a new quinolone derivate compared with those of other antimicrobial agents. Antimicrobial Agents and Chemotherapy 23(4), pp. 559-564.

Yim, D. et al., "The Development of Inhaled Liposome-Encapsulated Ciprofloxacin to Treat Cystic Fibrosis," Respiratory Drug Delivery, pp. 425-428 (2006).

Zhang, X. et al., "Antibacterial drug treatment of community acquired pneumonia," Chinese Journal of Respiratory and Critical Care Medicine, 4(4):258-260 (2005).

\* cited by examiner

Amikacin

Gentamicin

Kanamycin

Neomycin

Vancomycin

Netilmicin

Paromycin

Streptomycin

Tobramycin

Apramycin

COMPOSITIONS OF MULTICATIONIC DRUGS FOR REDUCING INTERACTIONS WITH POLYANIONIC BIOMOLECULES AND METHODS OF USE THEREOF

RELATED APPLICATION

This application is a continuation of U.S. patent application Ser. No. 12/598,830, filed Apr. 7, 2010, which is the National Stage Entry of International Patent Application No. PCT/US2008/62469, filed May 2, 2008, which claims the benefit of priority to U.S. Provisional Patent Application No. 60/916,002, filed on May 4, 2007, each of which is hereby incorporated by reference in their entireties.

BACKGROUND OF THE INVENTION

The most consistent aspect of therapy for pulmonary diseases such as, for example, cystic fibrosis (CF), is limiting and treating the lung damage caused by thick mucus and infection with the goal of maintaining quality of life.

Cystic fibrosis is a life-threatening, inherited disorder caused by an abnormality in the cystic fibrosis transmembrane conductance regulator (CFTR) and characterized by chronic progressive lung disease. Abnormal function of CFTR (and other ion channels) leads to inspissated static mucus in the lungs and a situation where mucociliary clearance and other antimicrobial defenses are damaged. The damage is so extensive that persistent infection by a predictable set of pathogens, especially *Pseudomonas aeruginosa*, and a concomitant chronic neutrophilic inflammatory response are characteristic consequences which are usually fatal. Pilewski, J. M. and Frizzell, R. A. (1999) Physiol. Rev. 79 (suppl. 1), 5215-5255; Chmiel, J. F. and Davis. P. B. (2003) State of the Art: Why do the lungs of patients with cystic fibrosis become infected and why can't they clear the infection? Resp. Res. 4, 8-20; Gibson, R. L., Burns, J. L. and Ramsey, B. W. (2003) Pathophysiology and management of pulmonary infections in cystic fibrosis. Am. J. Respir. Crit. Care Med. 168, 918-951.

*P. aeruginosa* grows in microcolonics with biofilm-like characteristics in the hypoxic environment of such stationary mucus where the bacterial cells elaborate a quorum-sensing system to control gene expression specifically for growth as a biofilm. Singh, P. K., Schaefer, A. L., Parsek, M. R., Moninger, T. O., Welsh, M. J. and Greenberg, E. P. (2000) Quorum-sensing signals indicate that cystic fibrosis lungs are infected with bacterial biofilms. Nature 407, 762-764; Parsek, M. R. and Greenberg, E. P. (2000) Acyl-homoserine lactone quorum sensing gram-negative bacteria: A signaling mechanism involved in associations with higher organisms. Proc. Nat. Acad. Sci. 97, 6789-6793. Observation of tissue samples from cystic fibrosis patients indicates that the *P. aeruginosa* is predominantly intraluminal, localized in hypoxic mucopurulent masses. Worlitzsch, D., Tarran, R., Ulrich, M., Schwab, U., Cekici, A., Meyer, K. C., Birrer, P., Bellon, G., Berger, J., Weiss, T., Botzenhart, K., Yankaskas, J. R., Randell, S., Boucher, R. C. and Doring, G. (2002) Effects of Reduced Mucus Oxygen Concentrations in Airway *Pseudomonas* infections of Cystic Fibrosis Patients. J. Clin. Invest. 109, 317-325. This environment may include a matrix composed of alginate or other exopolysaccharides from mucoid bacteria, mucins from lung epithelial cells and DNA from damaged leukocytes. Costerton, J. W., Stewart, P. S., and Greenberg, E. P. (1999) Bacterial Biofilms: A Common Cause of Persistent Infections, Science 284:1318-1322. Alginate production by *P. aeruginosa* is actually stimulated in such hypoxic conditions, converting non-mucoid versions to mucoid. Worlitzsch, D., Tarran, R., Ulrich, M., Schwab, U., Cekici, A., Meyer, K. C., Birrer, P., Bellon, G., Berger, J., Weiss, T., Botzenhart, K., Yankaskas, J. R., Randell, S., Boucher, R. C. and Doring, G. (2002) Effects of Reduced Mucus Oxygen Concentrations in Airway *Pseudomonas* infections of Cystic Fibrosis Patients. J. Clin. Invest. 109, 317-325; Sabra W., Kim E. J., Zeng A. P. (2002) Physiological responses of *Pseudomonas aeruginosa* PAO1 to oxidative stress in controlled microaerobic and aerobic cultures. Microbiology 148, 3195-3202.

The biofilm-like mode of growth results in a difficult challenge for antibiotic therapy. For aminoglycosides, slow penetration and lack of activity against cells in a slow growth phenotype are particularly important. Mendelman, P. M. et al., "Aminoglycoside Penetration, Inactivation, and Efficacy in Cystic Fibrosis Sputum," Am. Rev. Respir. Div. 1985, 132(4), 761-5; Hunt, B. E. et al. "Macromolecular Mechanisms of Sputum inhibition of Tobramycin Activity," Antimicrob. Agents Chemother., 1995, 39(1), 34-9; Chambless, J. D., Hunt, S. M. and Stewart, P. S. (2006). A three-dimensional computer model of four hypothetical mechanisms protecting biofilms from antimicrobials. Appl Environ Microbiol 72, 2005-13. To make matters worse, subinhibitory levels of aminoglycosides help to induce biofilm formation. Drenkard, E. and Ausubel, F. M. (2002) *Pseudomonas* biofilm formation and antibiotic resistance are linked to phenotypic variation. Nature 416, 740-743; Hoffman, L. R., D'Argenio, D. A., MacCoss, M J., Zhang, Z., Jones, R. A. and Miller, S. I. (2005). Aminoglycoside antibiotics induce bacterial biofilm formation. Nature 436, 1171-1175. One approach to increase efficacy in this situation has been direct administration of antibiotics to the lungs via inhalation. However, because of the small size and charged nature of these drugs, they are rapidly removed from the lungs after inhalation, limiting the amount of time they remain at a concentration above the effective minimum inhibitory concentration. P. P. H. LeBrun et al: Pharmcokinetic modeling of tobramycin after high dose inhalation in patients with cystic fibrosis. In: "*Optimization of antibiotic inhalation therapy in cystic fibrosis*" Ph.D. thesis, Rijksuniversiteit Groningen, 2001, Chapter 7; J. S. Patton, C. S. Fishburn, and J. G. Weers. The lungs as a portal of entry for systemic drug delivery. Proc. Am. Thor. Soc. 1:338-344 (2004). The charged nature of many of the antibiotics used in these applications also inhibits their penetration of the predominantly anionic biofilms that form in many pulmonary diseases.

Pneumonia is an illness of the lungs and respiratory system in which the alveoli (microscopic air-filled sacs of the lung responsible for absorbing oxygen from the atmosphere) become inflamed and flooded with fluid. Pneumonia can result from a variety of causes, including infection with bacteria, viruses, fungi, or parasites. Pneumonia may also occur from chemical or physical injury to the lungs, or indirectly due to another medical illness, such as lung cancer or alcohol abuse.

Antibiotics are given whenever *pneumonia* is suspected or to treat bacterial infections associated with cystic fibrosis resulting in a decline in lung function. Antibiotics are often chosen based on information about prior infections. Many bacteria common in pulmonary distress are resistant to multiple antibiotics and require weeks of treatment with intravenous antibiotics such as amikacin, vancomycin, tobramycin, meropenem, ciprofloxacin, and piperacillin. This prolonged therapy often necessitates hospitalization and insertion of a more permanent IV such as a PICC line or Port-a-Cath. Inhaled therapy with antibiotics such as tobramycin and colistin is often given for months at a time in order to improve lung function by impeding the growth of colonized bacteria. Pai V B, Nahata M C. *Efficacy and safety of aerosolized tobramycin in cystic fibrosis*. Pediatr Pulmonol. 2001 October; 32(4):314-27. Review; Westerman E M, Le Brun P P, Touw D J, Frijlink H W, Heijerman H G. *Effect of nebulized colistin sulphate and colistin sulphomethate on lung function in patients with cystic fibrosis: a pilot study*. J Cyst Fibros. 2004 March; 3(1):23-8. Oral antibiotics such as ciprofloxacin or azithromycin are sometimes given to help prevent infection or to control ongoing infection. Hansen C R, Pressler T, Koch C, Hoiby N. *Long-term azithromycin treatment of cystic fibrosis patients with chronic Pseudomonas aeruginosa infection; an observational cohort study*. J Cyst Fibros. 2005 March; 4(1):35-40. Some individuals spend years between hospitalizations for antibiotics, while others require several antibiotic treatments each year.

Improved antibiotic compositions are needed that overcome the problem of biofilm penetration due to the oppositely charged multicationic drug and polyanionic biofilm.

SUMMARY OF INVENTION

It is an object of the present invention to increase the bioactivity of a multicationic drug by reducing drug binding to polyanionic biomolecules. It is also an object of the present invention to treat a subject for pulmonary distress by administering a multicationic drug that has a reduced binding affinity with polyanionic biomolecules. It is another object of the present invention to provide a kit comprising a multicationic drug with a reduced binding affinity for polyanionic biomolecules.

The present invention results from the realization that the presence of an organic multianion reduces the binding affinity of multicationic drugs to polyanionic biomolecules.

In one aspect, the present invention relates to a composition comprising a multicationic drug and an organic multianion. In a further embodiment, the multicationic drug is enclosed within a carrier. In a further embodiment, the multicationic drug and organic multianion are enclosed within a carrier. In a further embodiment, the multicationic drug is enclosed within a carrier and the organic multianion is outside the carrier. In a further embodiment, the carrier is a liposome. In a further embodiment, the liposome comprises a phospholipid. In a further embodiment, the liposome comprises a sterol. In a further embodiment, the liposome comprises a lipid selected from the group consisting of egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic aicd (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic aicd (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleylphosphatidyl-ethanolamine (DOPE), palmitoylstearoylphosphatidyl-choline (PSPC), palmitoylstearolphosphatidylglycerol (PSPG), mono-oleoyl-phosphatidylethanolamine (MOPE), cholesterol, ergosterol, lanosterol, tocopherol, ammonium salts of fatty acids, ammonium salts of phospholipids, ammonium salts of glycerides, myristylarnine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA), 1,2-bis(oleoyloxy)-3-(trimethylammonio)propane (DOTAP), phosphatidyl-glycerols (PGs), phosphatidic acids (PAs), phosphatidylinositols (Pls), phosphatidyl serines (PSs), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphospatidylinositol (DSPI), dimyristoylphosphatidylserine (DMPS), dipalmitoylphosphatidylserine (DPPS), distearoylphosphatidylserine (DSPS), and mixture thereof. In a further embodiment, the liposome comprises a phospholipid and a sterol. In a further embodiment, the liposome comprises DPPC and cholesterol.

In a further embodiment, the multicationic drug is an aminoglycoside. In a further embodiment, the multicationic drug is selected from the group consisting of amikacin, gentamicin, kanamycin, neomycin, vancomycin, netilmicin, paromomycin, streptomycin, tobramycin, and aparmycin.

In a further embodiment, the organic multianion is selected from the group consisting of citrate, maleate, tartarate, glutarate, succinate, malonate, adipate, pimelate, suberate, azelate, sebacate, and terephthalate.

In a further embodiment, the organic multianion is selected from the group consisting of citrate, maleate, tartarate, glutarate, succinate, malonate, adipate, pimelate, suberate, azelate, sebacate, and terephthalate, and the multicationic drug is selected from the group consisting of amikacin, gentamicin, kanamycin, neomycin, netilmicin, paromomycin, streptomycin, tobramycin, and aparmycin. In a further embodiment, the multicationic drug is amikacin and the organic multianion is citrate. In a further embodiment, the multicationic drug is amikacin, the organic multianion is citrate, and the liposome comprises DPPC and cholesterol.

In a further embodiment, the composition further comprises an inhalation device. In a further embodiment, the composition is in the form of a liquid. In a further embodiment, the liquid is an aqueous solution. In a further embodiment, the composition is in the form of a solid. In a further embodiment, the solid is a powder, film, or paste.

In a further embodiment, the concentration of anionic groups of the organic multianion is at least 10 mM. In a further embodiment, the concentration of anionic groups of the organic multianion is at least 30 mM. In a further embodiment, the concentration of anionic groups of the organic multianion is at least 100 mM.

In another aspect, the present invention relates to a method of treating a subject for pulmonary distress comprising administering to the subject in need thereof an effective amount of the composition of the present invention. In a further embodiment, the pulmonary distress is cystic fibrosis or pneumonia. In a further embodiment, the pulmonary distress is cystic fibrosis. In a further embodiment, the subject is a mammal. In a further embodiment, the subject is a human, primate, equine, bovine, porcine, canine, feline, or rodent. In a further embodiment, the subject is a human.

In another aspect, the present invention relates to a kit comprising the composition of the present invention, an inhalation device, and directions for use thereof.

These embodiments of the present invention, other embodiments, and their features and characteristics, will be apparent from the description, drawings and claims that follow.

DETAILED DESCRIPTION OF INVENTION

I. Definitions

Figure 1:
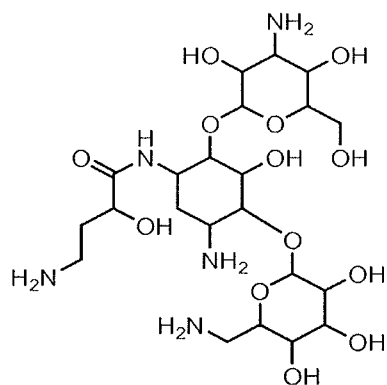
FIGS. 1 and 2 depict the structures of aminoglycosides.
Figure 1:
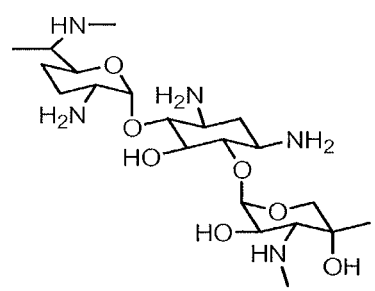
Figure 1:
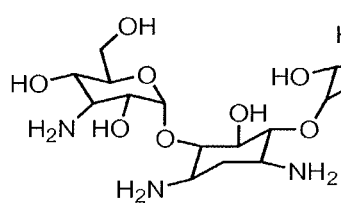
Figure 1:
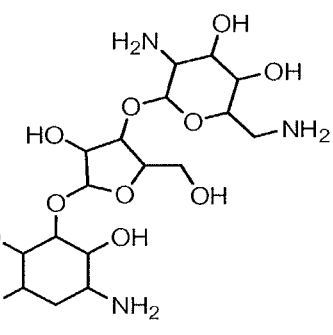
Figure 1:
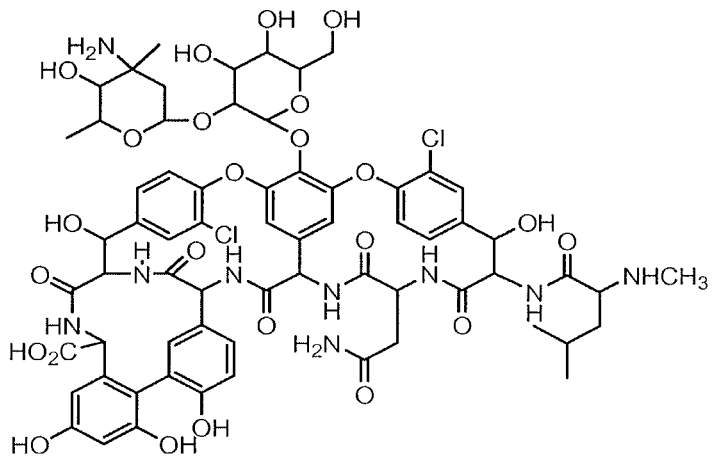

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The suffix "ic" in chemical nomenclature refers to an acid, while the suffix "ate" refers to the anionic form of the acid after deprotonation. For instance "citric" refers to the acid and "citrate" refers to the anion after the acid has lost at least one proton. It is recognized that the acid and anion form of a compound coexist in equilibrium under most conditions.

The term "including" is used to mean "including but not limited to". "Including" and "including but not limited to" are used interchangeably.

The terms "Lewis base" and "Lewis basic" are art-recognized and generally include a chemical moiety, a structural fragment or substituent capable of donating a pair of electrons under certain conditions. It may be possible to characterize a Lewis base as donating a single electron in certain complexes, depending on the identity of the Lewis base, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions.

The term "proton" is used interchangeably with $H^+$. Thus a proton refers to $H^+$ dissociated from a Bronsted acid.

The term "pulmonary distress" refers to any disease, ailment, or other unhealthy condition related to the respiratory tract of a subject caused by an infecting agent. Generally pulmonary distress results in difficulty of breathing.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics,* 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The term "small molecule" is art-recognized and refers to a composition which has a molecular weight of less than about 2000 amu, or less than about 1000 amu, and even less than about 500 amu. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "treating" is art-recognized and refers to curing as well as ameliorating at least one symptom of any condition or disease.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

A "patient," "subject" or "host" to be treated by the subject method may mean either a human or non-human animal.

The term "mammal" is known in the art, and exemplary mammals include humans, primates, bovines, porcines, canines, felines, and rodents (e.g., mice and rats).

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Contemplated equivalents of the compositions described herein include compositions which otherwise correspond thereto, and which have the same general properties thereof, wherein one or more simple variations of substituents or components are made which do not adversely affect the characteristics of the compositions of interest. In general, the components of the compositions of the present invention may be prepared by the methods illustrated in the general reaction schema as, for example, described below, or by modifications thereof, using readily available starting materials, reagents and conventional synthesis procedures. In these reactions, it is also possible to make use of variants which are in themselves known, but are not mentioned here.

II. Introduction

Many drugs used for treating pulmonary distress contain more than one Lewis base capable of protonation under normal physiological conditions. The multicationic charge imparted to the drug impedes the drug's effectiveness in two ways. The increased polarity facilitates rapid removal of the drug from the lungs, and it increases drug binding to components of sputum, such as alginate (or other alginic acids) or DNA, which often makes up biofilms associated with many pulmonary diseases. Sputum is matter that is coughed up from the respiratory tract, such as mucus or phlegm, mixed with saliva and then expectorated from the mouth. It can also contain pus, blood, fibrin, bacterial products or other foreign matter. Alginic acid is a component of sputum produced by P. Aeruginosa biofilm. Alginate is a high MW anionic polymer that can be separated by filters with appropriate pore size.

Figure 2:
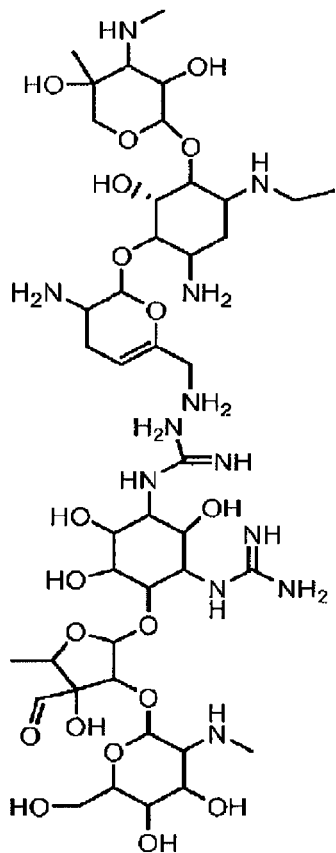
Figure 2:
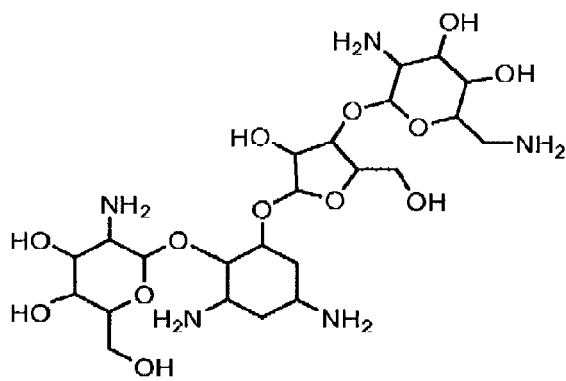
Figure 2:
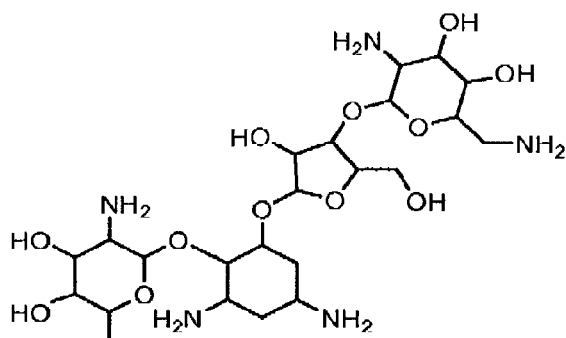
Figure 2:
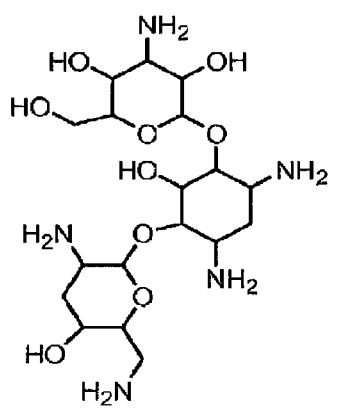
Figure 2:
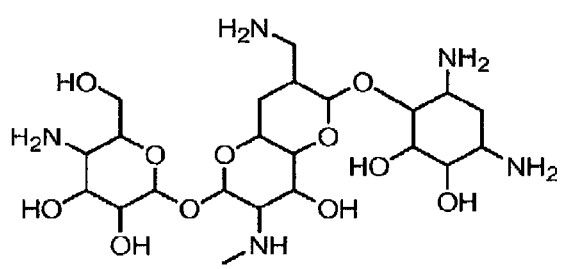

FIGS. 1 and 2 depict a class of antibiotics known as aminoglycosides. Note how each aminoglycoside includes several amine groups capable of protonation under normal physiological conditions. For example, the aminoglycoside amikacin commonly exists as a +4 cation:

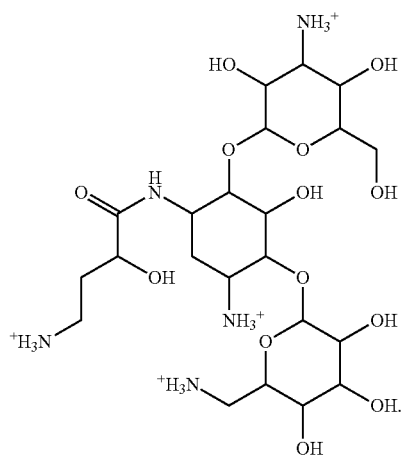

It has been suggested that the antibacterial efficiency of aminoglycosides is reduced because of its binding to sputum components such as alginate (or other acidic mucins) and DNA. Indeed, amikacin, having up to a +4 charge can have strong affinity to multianionic polymers.

The present invention allows increased drug bioactivity by reducing drug binding to the polyanionic components of sputum.

The presently disclosed formulations are superior in antibacterial efficiency when used to treat diseases that result in the formation of harmful multianionic polymers such as alginate and DNA in sputum. The liposome slows removal of the antibiotic from the site of distress and the salt of the multiprotonic acid reduces binding between the antibiotic and multianionic polymer. In one embodiment, the liposomal formulation comprises an antibiotic-multianion complex which after release from the liposome exhibits superior antibiotic efficiency when used in biological systems containing multianionic polymers such as alginate and DNA.

III. Results

The binding of a multicationic drug, such as amikacin, to alginate in presence salts of various (one-, two- and three-protonic) acids was tested. To study the effect of binding of amikacin to alginate, amikacin sulfate, Na citrate and Na alginate were mixed at different proportions and then free (unbound) amikacin was separated on a Cetricon-10 filtering device (MWCO 10 kD). In the absence of citrate, amikacin binds to alginate only, and the amikacin-alginate binding coefficient can be calculated from equation:

$$P_{alg} = \frac{[AMK]_{bound}}{[AMK]_{free} \times [Alg]} \qquad \text{Eq. 1}$$

where bound amikacin can be found by subtracting free from total, and alginate free concentration is assumed to be equal to the total concentration due to excess of alginate over amikacin. Results are reported in Table 1.

TABLE 1

Binding of amikacin to alginate in saline.*

| Alginate mg/mL | $AMK_{free}$ ug/mL | $AMK_{Alg}$ ug/mL | $AMK_{Alg}/AMK_f$ |
|---|---|---|---|
| 16 | 6.5 | 86 | 13.23 |
| 14 | 8 | 84.5 | 10.56 |
| 10 | 12.6 | 79.9 | 6.34 |
| 6 | 20 | 72.5 | 3.63 |
| 0 | 92.5 | 0 | 0 |
| $P_{Alg}$ AMK-Alginate $(mg/ml)^{-1}$ | | | 0.76 |

Figure 3:
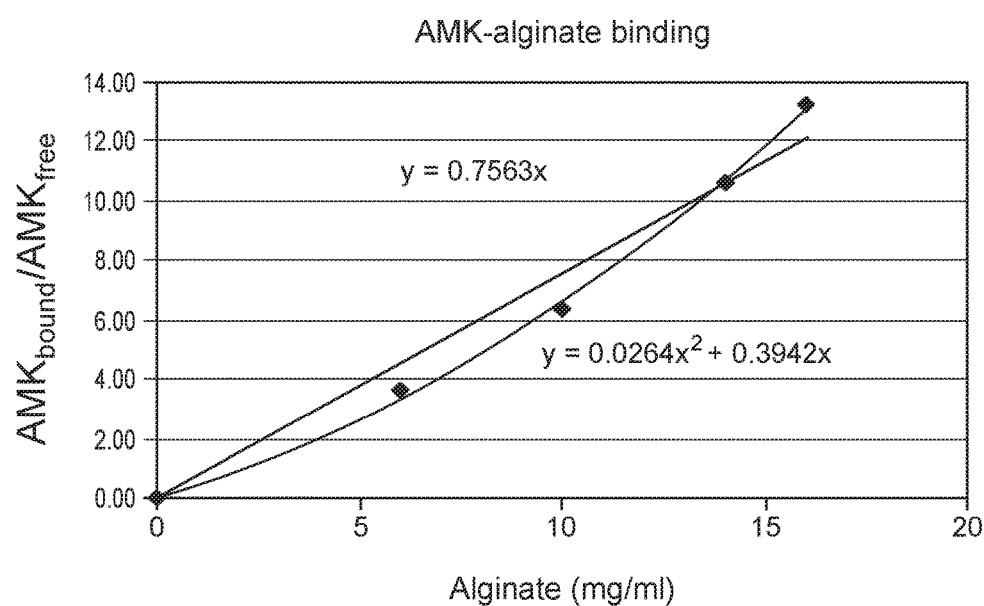
FIG. 3 depicts amikacin alginate binding. $AMK_{Alg}/AMK_f$ ratio is taken from Table 1.

*No citrate was added. Total amikacin added was 92.5 ug/mL. Bound amikacin was determined as $AMK_t-AMK_f$. Binding coefficient $P_{Alg}$ was found from the slope $AMK_{Alg}/AMK_f$ vs alginate concentration (see FIG. 3).

As alginate concentration increases, amikacin free measured in permeate decreases (Table 1). According to Equation 1 the ratio $AMK_{Alg}/AMK_f$ should be proportional to the concentration of alginate, and the slope of this dependence should equal to the binding coefficient. If plotted (FIG. 3), $AMK_{Alg}/AMK_f$ does not show a perfect linear dependence but rather can be fitted well with a quadratic regression. It suggests that there might be more complex interaction between amikacin and alginate molecules.

If one use a linear regression, the slope obtained gives us an estimate of the amikacin-alginate binding coefficient of $P_{Alg}=0.76$ $(mg/mL)^{-1}$. This means that in presence of $1/P_{Alg} \sim 1.3$ mg/mL alginate approximately half of all amikacin will be bound to alginate.

In the presence of citrate, amikacin can bind to both alginate and citrate. The amikacin-citrate complex is not large enough to be retained by Centricon filter and will be measured as "free" amikacin, which is actually a sum of free and citrate bound amikacin. For that reason amikacin-citrate binding can not be measured directly. It can, however, be determined indirectly from competitive binding, knowing amikacin-alginate binding coefficient $P_{Alg}$.

TABLE 2

Binding of amikacin to citrate.*

| Alginate mg/mL | Citrate mM | $AMK_{perm}$ ug/ml | $AMK_{Alg}$ | $AMK_{free}$ | $AMK_{citrate}$ | $AMK_{cit}/AMK_f$ |
|---|---|---|---|---|---|---|
| 16 | 10 | 10.1 | 82.4 | 6.81 | 3.29 | 0.48 |
| 14 | 20 | 15.5 | 77 | 7.27 | 8.23 | 1.13 |
| 10 | 40 | 32.0 | 60.5 | 8.00 | 24.00 | 3.00 |
| 6 | 60 | 51.6 | 40.9 | 9.01 | 42.59 | 4.72 |
| 0 | 0 | 92.5 | 0 | 92.5 | 0 | 0 |
| | | $P_{cit}$ AMK-Citrate $mM^{-1}$ | | | | 0.076 |

Figure 4:
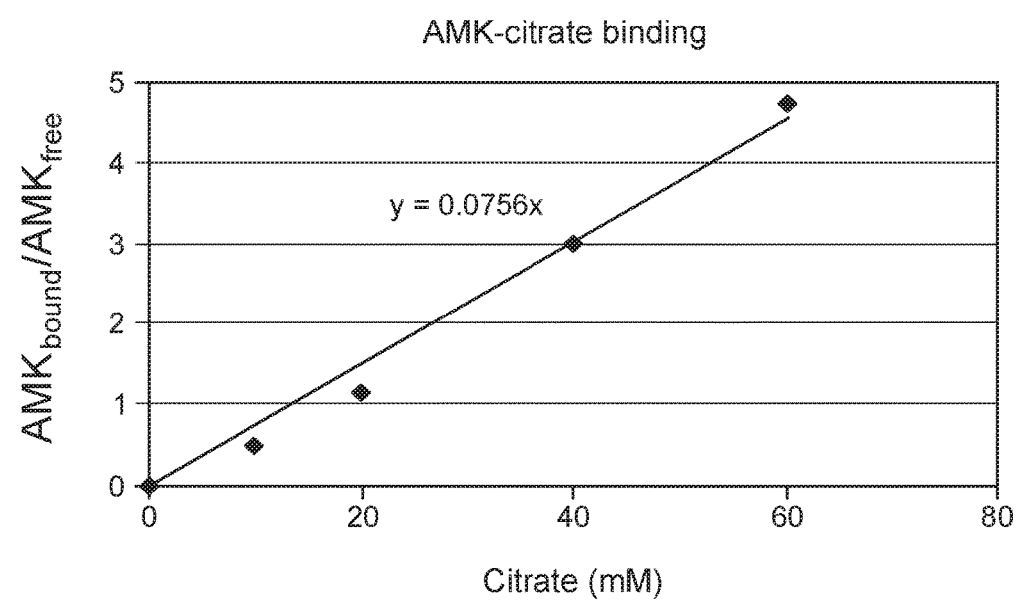
FIG. 4 depicts amikacin-citrate binding. $AMK_{cit}/AMK_f$ ratio is taken from Table 2.

*Both alginate and citrate were mixed with amikacin. Bound amikacin was determined as $AMK_{tot}-AMK_{perm}$. Binding coefficient $P_{cit}$ was found from the slope $AMK_{cit}/AMK_f$ vs citrate concentration (FIG. 4).

Amikacin-citrate binding coefficient was $P_{cit}=0.076$ $mM^{-1}$. Thus in the presence of $1/P_{cit} \sim 13$ mM citrate the concentration of amikacin bound to citrate is approximately equal to the concentration of free amikacin. As one can see from the above data, citrate can compete for amikacin with alginate thus reducing amount of amikacin bound to alginate. 1% Alginate can reduce AMK free concentration ~7-fold. Citrate at 40 mM reduces this effect increasing unbound AMK ~2.5 fold.

How pH affects the ability of citrate to compete with alginate for amikacin was also tested. Here 0.5 mL sodium alginate (2%) was mixed with 0.4 mL sodium citrate (200 mM) and 0.1 mL amikacin sulfate (1 mg/mL), giving corresponding final concentrations of 1%, 80 mM, and 100 ug/mL, respectively. Two controls using either alginate or citrate alone were employed. Samples were incubated for 10 minutes at 37° C. and unbound amikacin was separated by centrifuging in Centrico-10 device for 30 minutes at 4000 rpm. Amikacin in permeate was measured by TDX (Abbott) and presented as % of total (Table 3).

TABLE 3

Effect of pH on amikacin-citrate binding.

| Samples | Amikacin not bound to alginate (%) |
|---|---|
| Alg + Citrate pH 5 | 56.4 |
| Alg + Citrate pH 6 | 70.4 |
| Alg + Citrate pH 7 | 68.1 |
| Alg, no Citrate | 11.9 |
| Alg, no Citrate, AMK 0.5 mg/mL | 14.5 |
| Citrate, no Alginate | 100 |

From the results in Table 3 citrate binding is most effective at near neutral pH 6-7, while at pH 5 less amikacin was found in permeate (more bound to alginate). In the absence of citrate, Alginate 1% binds ~88% AMK, leaving only 12% in permeate. 80 mM Citrate at pH 6-7 reduces binding to ~30% increasing unbound AMK to ~70%. Additional samples had no citrate but did have increased concentrations of total amikacin (0.5 mg/mL). Alginate binding efficiency was 85.5%, almost unchanged from control sample with 0.1 mg/mL amikacin. This shows that the binding capacity of alginate is at least 0.05 mg amikacin per mg alginate. This binding capacity is sufficient to reduce amikacin activity in real in-vivo conditions.

Various salts were tested for their ability to compete with alginate. Amikacin sulfate (0.1 mL of 1 mg/ml) was added to 0.4 mL solution of 1% Na Alginate and 0.5 mL solution of 200 mM Na salt of an Acid at pH 6.0. Samples were incubated 10 minutes at 37° C. and centrifuged in Centricon-10 for 30 minutes at 4000 rpm. Filtrate was diluted 2 fold with TDX buffer and analyzed for AMK.

TABLE 4

Effect of mono- and multi-protonic acid salts on binding of amikacin to alginate.

| Sample | Amikacin not bound to alginate (%) |
|---|---|
| Sodium citrate | 72.1 |
| Sodium maleate | 39.4 |
| Sodium tartarate | 41.4 |
| Sodium glutarate | 36.7 |
| Sodium succinate | 40.2 |
| Sodium acetate | 11.2 |
| Control | 17.7 |

It was surprisingly found that citrate was the most efficient in reducing amikacin-alginate binding, showing 72.1% unbound amikacin in permeate. All two-protonic acids (maleate, taratrate, glutarate, succinate) were able to produce nearly similar ~40% unbound amikacin. Mono-protonic acetate was the least effective, not showing any increase in unbound amikacin (in fact it decreased the amount of unbound amikacin).

It has been shown elsewhere (ref) that amikacin-alginate binding can in fact reduce amikacin bioactivity against PA. One may ask whether binding to citrate will preserve bioactivity or inhibit it similar to alginate. In order to address this, activity of amikacin against *P. Aeruginosa* PAC1 using modified disk Kirby-Bauer agar diffusion method was tested. PA was grown on MH medium supplemented with Alginate, Na acetate, or a combination thereof. Absence of supplements was used as a control. Free-growth zone size was measured in each sample and presented in Table 5.

TABLE 5

In-Vitro bioactivity of amikacin against PA in presence of alginate and citrate.

| Sample | Zone size (mm) | | |
|---|---|---|---|
| Control | 28 | 29 | 28 |
| Alginate 1% | 21 | 21 | 21 |
| Citrate 100 mM | 28 | 28 | 28 |
| Alginate + Citrate | 28 | 29 | 28 |

Activity was determined using modified disk Kirby-Bauer agar diffusion method and PAC1 PA strain. The data clearly show that Alginate dose reduce bioactivity of amikacin reducing zone size from 28 to 21 mm. Citrate at concentration 100 mM does not affect activity. Moreover, when both alginate and citrate were present, citrate actually restored activity of amikacin.

IV. Organic Multianions

The organic multianions are generally prepared from multiprotonic acids having more than one acid group on the molecule. Examples of organic multiprotonic acids include, but are not limited to, maleic, tartaric, glutaric, succinic, malonic, adipic, pimelic, suberic, azelaic, sebacic, and terephthalic acid. The above acids form salts through dissociation of a proton. Many of the above acids are available commercially in salt form such as, for example, a sodium salt. If a multiprotonic acid is not available as a salt, one of ordinary skill in the art can easily prepare the salt by reacting the multiprotonic acid with an effective amount of a base such as, for example, NaOH, KOH, LiOH, NaHCO$_3$, or Na$_2$CO$_3$.

When starting with the polyprotonic acid already in salt form, compositions of the present invention can be prepared in one embodiment by reacting the salt with the multicationic drug. For example, when the multicationic drug is amikacin +4, one can react the amikacin with enough sodium citrate to displace at least some of the existing counterion and replace it with citrate anion. Alternatively, one of ordinary skill in the art can partially form the compositions of the present invention by reacting the drug in its neutral state with the multiprotonic acid. For example, one can react amikacin in the neutral state with enough citric acid to protonate at least some of the amine groups to form a multicationic —NH$_3^+$ group with the citrate as the counterion.

V. Multicationic Drug

In one embodiment, the multicationic drug is a multicationic antibiotic. The antibiotic generally comprises a Lewis base that is protonated under normal physiological conditions. Multicationic antibiotics covered by the invention include but are not limited to aminoglycosides (e.g., streptomycin, gentamicin, tobramycin, amikacin, netilmicin, vancomycin, kanamycin, and the like), tetracyclines (such as chlortetracycline, oxytetracycline, methacycline, doxycycline, minocycline and the like), sulfonamides (e.g., sulfanilamide, sulfadiazine, sulfamethaoxazole, sulfisoxazole, sulfacetamide, and the like), paraaminobenzoic acid, diaminopyrimidines (such as trimethoprim, often used in conjunction with sulfamethoxazole, pyrazinamide, and the like), quinolones (such as nalidixic acid, cinoxacin, ciprofloxacin and norfloxacin and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil; cefmetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), beta-lactamase inhibitors (such as clavulanic acid), chlorampheriicol, macrolides (such as erythromycin, azithromycin, clarithromycin, and the like), lincomycin, clindamycin, spectinomycin, polymyxin B, polymixins (such as polymyxin A, B, C, D, E1 (colistin A), or E2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated.

In certain embodiments, the multicationic drug is an antifungal agent, including polyene antifungals (such as amphotericin B, nystatin, natamycin, and the like), flucytosine, imidazoles (such as n-ticonazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed. Discussion and the examples are directed primarily toward amikacin but the scope of the application is not intended to be limited to this antiinfective. Combinations of drugs can be used.

In one embodiment, multicationic drugs include aminoglycosides, quinolones, polyene antifungals and polymyxins. In one embodiment, aminoglycosides include amikacin, gentamicin, vancomycin, and tobramycin.

In cases wherein the compounds may have one or more chiral centers, unless specified, the present invention comprises each unique racemic compound, as well as each unique nonracemic compound.

In cases in which the drugs have unsaturated carbon-carbon double bonds, both the cis (Z) and trans (E) isomers are within the scope of this invention. In cases wherein the drugs may exist in tautomeric forms, such as keto-enol tautomers, such as

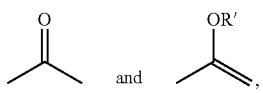

each tautomeric form is contemplated as being included within this invention, whether existing in equilibrium or locked in one form by appropriate substitution with R'. The meaning of any substituent at any one occurrence is independent of its meaning, or any other substituent's meaning, at any other occurrence.

Also included as suitable multicationic drugs used in the compositions of the present invention are prodrugs of the drug compounds. Prodrugs are considered to be any covalently bonded carriers which release the active parent compound in vivo.

VI. Carrier

The carrier of the present invention may be any substance capable of supporting or containing the multicationic drug. Non-limiting examples of carriers include polymers and copolymers, micelles, reverse micelles, liposomes, microspheres, emulsions, hydrogels, microparticles, nanoparticles, colloids and solid surfaces. In one embodiment, the carrier is biocompatible.

(i) Polymers and Co-Polymers

In certain embodiments, the polymers or co-polymers of the subject compositions, e.g., which include repetitive elements shown in any of the subject formulas, have molecular weights ranging from about 2000 or less to about 1,000,000 or more Daltons, or alternatively about 10,000, 20,000, 30,000, 40,000, or 50,000 Daltons, more particularly at least about 100,000 Daltons, and even more specifically at least about 250,000 Daltons or even at least 500,000 Daltons. Number-average molecular weight (Mn) may also vary widely, but generally fall in the range of about 1,000 to about 200,000 Daltons, or even from about 1,000 to about 100,000 Daltons or even from about 1,000 to about 50,000 Daltons. In one embodiment, Mn varies between about 8,000 and 45,000 Daltons. Within a given sample of a subject polymer, a wide range of molecular weights may be present. For example, molecules within the sample may have molecular weights which differ by a factor of 2, 5, 10, 20, 50, 100, or more, or which differ from the average molecular weight by a factor of 2, 5, 10, 20, 50, 100, or more.

One method to determine molecular weight is by gel permeation chromatography ("GPC"), e.g., mixed bed columns, $CH_2Cl_2$ solvent, light scattering detector, and off-line dn/dc. Other methods are known in the art.

In certain embodiments, the intrinsic viscosities of the polymers generally vary from about 0.01 to about 2.0 dL/g in chloroform at 40° C., alternatively from about 0.01 to about 1.0 dL/g and, occasionally, from about 0.01 to about 0.5 dL/g.

The glass transition temperature (Tg) of the subject polymers may vary widely, and depend on a variety of factors, such as the degree of branching in the polymer components, the relative proportion of phosphorous-containing monomer used to make the polymer, and the like. When the article of the invention is a rigid solid, the Tg is often within the range of from about −10° C. to about 80° C., particularly between about 0 and 50° C. and, even more particularly between about 25° C. to about 35° C. In other embodiments, the Tg is low enough to keep the composition of the invention flowable at body temperature. Then, the glass transition temperature of the polymer used in the invention is usually about 0 to about 37° C., or alternatively from about 0 to about 25° C.

In other embodiments, the polymer composition of the invention may be a flexible or flowable material. When the polymer used is itself flowable, the polymer composition of the invention, even when viscous, need not include a biocompatible solvent to be flowable, although trace or residual amounts of biocompatible solvents may still be present.

A flexible polymer may be used in the fabrication of a solid article. Flexibility involves having the capacity to be repeatedly bent and restored to its original shape. Solid articles made from flexible polymers are adapted for placement in anatomic areas where they will encounter the motion of adjacent organs or body walls. A flexible solid article can thus be sufficiently deformed by those moving tissues that it does not cause tissue damage. Flexibility is particularly advantageous where a solid article might be dislodged from its original position and thereby encounter an unanticipated moving structure; flexibility may allow the solid article to bend out of the way of the moving structure instead of injuring it. Such a flexible article might be suitable for covering pulsatile vessels such as the carotid artery in the neck, or for covering more delicate structures in the neck like the jugular vein that may also be affected by local movements. Similarly, a flexible solid article may be used to protect nerves exposed during a neck dissection such as the spinal accessory nerve, wherein the flexibility of the solid article may permit it to bend or deform when encountering motion rather than eroding into or damaging the nerve. Use of a solid carrier according to the present invention in the aforesaid ways may allow less extensive dissections to be carried out with surgical preservation of structures important to function. Solid articles may be configured as three-dimensional structures suitable for implantation in specific anatomic areas. Solid articles may be formed as films, meshes, sheets, tubes, or any other shape appropriate to the dimensions and functional requirements of the particular anatomic area. Physical properties of polymers may be adjusted to attain a desirable degree of flexibility by modification of the chemical components and crosslinking thereof, using methods familiar to practitioners of ordinary skill in the art.

Examples of polymeric carriers include carboxylated or carboxymethylated linear poly-1-lysine (PL) or poly-D-lysine; carboxylated or carboxymethylated poly-alpha, beta-(2-aminoethyl)-D,L-aspartamide; poly-1-aspartic acid; poly-glutamic acid, copolymers of histidine with positively or negatively charged aminoacids, carboxylated polyethyleneimines, i.e. polyethylene imines reacted with derivatives of carbonic acids; natural saccharides or products chemically derived thereof, bearing carboxylic groups, which may be exemplified by: galacturonic acid, glucuronic acid, mannuronic acid, hyaluronic acid, pectic acid, neuraminic acid, alginic acid, carrageenan; oxidized dextrans; aminated, e.g. containing linked amino groups, polysaccharides or oligosaccharides, linear or branched; carboxylated, carboxymethylated, sulfated or phosphorylated polysaccharides or oligosaccharides, e.g. reacted with derivatives of carbonic, dicarbonic, sulfuric, aminosulfuric, phosphoric acids with resultant linking of carboxylic, aminocarboxylic, carboxymethyl, sulfuric, amino or phosphate groups. Such olygosaccharides may be obtained by chemical alteration of e.g., dextran, mannan, xylan, pullulan, cellulose, chytosan, agarose, fucoidan, galactan, arabinan, fructan, fucan, chitin, pustulan, levan or pectin. In addition these poly- or oligosachharides may be represented by heteropolymers or homopolymers of monosaccharides such as glucose, galactose, mannose, galactose, deoxyglucose, ribose, deoxyribose, arabinose, fucose, xylose, xylulose, ribulose, polyamidoamine, linear or branched; polyacrylic acid; polyalcohols, e.g. polyvinylalcohol an polyxylitol, to which carboxylic or amino groups are chemically linked. The molecular weight of a polyaminoacid is preferably larger than 1000 and smaller than 100000. Polyamino acids with narrow molecular weight (MW) distribution are preferred to those with broad MW distribution. Polyamino acids are linked with peptide bonds. Polyaminoacids are prepared by chemical synthesis or by recombinant techniques, such as genetic engineering. For additional examples of polymers suitable for use in the present invention see U.S. Pat. Nos. 6,509,323; 6,492,560; 6,468,532; 6,521,736; 6,348,069; 5,871,710; and 6,051,549. In another embodiment, the polymer acting as the carrier may be poly(ethylene glycol) (PEG) with functional groups at the far-end making up the metal binding domain to which the metal ion coordinates and in turn coordinates the active agent. Schematically the embodiment may be represented by the following: PEG-MBD-Metal-MBD-Active agent. Alternatively, PEG may be functionalized along its backbone allowing MBD-Metal-MBD-Active agent moieties to be pendant to the backbone. This functionalization may also allow pendant protective chains as well.

(ii) Micelles, Reverse Micelles, Liposomes and Microspheres

Amphipathic compounds that contain both hydrophobic and hydrophilic domains are typically organized into vesicular structures such as liposomes, micellar, or reverse micellar structures. Liposomes can contain an aqueous volume that is entirely enclosed by a membrane composed of lipid molecules (usually phospholipids). Micelles and reverse micelles are microscopic vesicles that contain amphipathic molecules but do not contain an aqueous volume that is entirely enclosed by a membrane. In micelles the hydrophilic part of the amphipathic compound is on the outside (on the surface of the vesicle) whereas in reverse micelles the hydrophobic part of the amphipathic compound is on the outside. The reverse micelles thus contain a polar core that can solubilize both water and macromolecules within the inverse micelle. As the volume of the core aqueous pool increases the aqueous environment begins to match the physical and chemical characteristics of bulk water. The resulting inverse micelle can be referred to as a microemulsion of water in oil.

In water, when a sufficient concentration of the two or more components that make up a micelle is present, the components spontaneously aggregate into thermodynamically stable polymeric micelles. The micelle particles assume a microspheroidal shape and possess, in essence, a double layer. The core "layer" forms by virtue of the hydrophobic interactions between, for example, hydrophobic polyesters. Similarly, the surface "layer" forms by virtue of the corresponding hydrophilic interactions of a, for example, hydrophilic polycation with water. A net positive charge will exist around the surface of the micelle, since the hydrophilic segment of the first component is a polycation.

Functional compounds having metal binding properties can be easily introduced to the micelle by: (1) creating a third copolymer component that bears the functional group and (2) coupling the copolymer to the surface of a pre-assembled polymeric micelle. Alternatively, a metal binding domain-bearing component can be incorporated into a micelle at the time the micelle originally forms. If so, then it may be preferable to use a copolymer wherein the metal binding domain resides in the hydrophilic segment so that it is exposed in the micelle surface layer. It is an advantage of the present invention that the kind and content of the functional group can be easily changed without limitation.

Micelles according to the present invention may comprise biodegradable, biocompatible copolymers, resulting in non-immunogenicity and non-toxicity. In one aspect copolymers disclosed herein degrade into non-toxic, small molecules subject to renal excretion and are inert during the required period of treatment. Degradation may occur via simple hydrolytic and/or enzymatic reaction. Degradation through simple hydrolysis may be predominant when the backbone of a copolymer comprises ester bonds. Enzymatic degradation may become significant in the presence of certain organelles such as liposomes. The degradation period can be varied from days to months by using polymers of different kinds and molecular weights. In one example, the present invention may use biodegradable polyesters or polypeptides possessing safe and biocompatible degradation pathways. In addition, the highly-branched micellar structure of the present invention may further reduce cytotoxicity since branched polycations such as dendritic polyamidoamines are thought to be less cytotoxic than linear polycations. Accordingly, the advantageous components and structure of polymeric micelles according to the present invention can be appreciated regarding reduced cytotoxicity. For additional examples of micelles, reverse micelles, liposomes, and microspheres suitable for the present invention see U.S. Pat. Nos. 6,338,859, 5,631,018; 6,162,462; 6,475,779; 6,521,211; and 6,443,898.

(iii) Emulsions and Hydrogels

Emulsions as the carrier in the present invention relate to emulsions of an aqueous or an aqueous-organic continuous phase and an organic discontinuous phase, the latter containing an organic solvent which is not miscible with water. Hydrogels are similar and refer to a type of gel in which the disperse phase has combined with water to produce a semisolid material. The emulsions and hydrogels used in the present invention may contain organic compounds from the group of the reaction products of alkylene oxides with compounds capable of being alkylated, such as, for example, fatty alcohols, fatty amines, fatty acids, phenols, alkylphenols, carboximides and resinic acids, preferably balsamic resin and/or abiotic acid.

Organic solvents which are not miscible with water include, for example, aliphatic, cycloaliphatic or aromatic hydrocarbons or the acetate-type solvents. Suitable as organic solvents are, preferably, natural, fully- or semisynthetic compounds and, if appropriate, mixtures of these solvents which are fully miscible or soluble with the other compounds of the emulsion in the temperature range of from 20 to 130° C. In one embodiment, suitable solvents are those from the group of the aliphatic, cycloaliphatic or aromatic hydrocarbons which are liquid at room temperature, including oils, such as, for example, mineral oils, paraffins, isoparaffins, fully-synthetic oils such as silicon oils, semisynthetic oils based on, for example, glycerides of unsaturated fatty acids of medium chain length, essential oils, esters of natural or synthetic, saturated or unsaturated fatty acids, for example $C_8$-$C_{22}$-fatty acids, $C_8$-$C_{18}$-fatty acids, especially preferably methyl esters of rapeseed oil or 2-ethylhexyl laurate, alkylated aromatics and their mixtures, alkylated alcohols, in particular fatty alcohols, linear, primary alcohols obtained by hydroformylation, terpene hydrocarbons and naphthene-type oils, such as, for example, Enerthene. Further organic solvents include those from the group of the acetate-type solvents such as, for example, 1,2-propanediol diacetate, 3-methyl-3-methoxybutyl acetate, ethyl acetate and the like. The solvents can be employed individually or as mixtures with each other.

The continuous aqueous or aqueous-organic phase of the active-agent-containing emulsions or microemulsions according to the present invention contain water, an organic solvent that is soluble or miscible in water, and may also contain at least one natural or synthetic surface-active agent which has a solubility of >10 g/l, in particular >100 g/l in water (d) at 20° C., and, if appropriate, further adjuvants.

Organic solvents which are soluble or miscible in water have a solubility in water of >5.0 g/l at 20° C., in particular >15 g/l.

Examples of suitable organic solvents are: aliphatic $C_1$-$C_4$-alcohols such as methanol, ethanol, isopropanol, n-propanol, n-butanol, isobutanol or tert-butanol, aliphatic ketones such as acetone, methyl ethyl ketone, methyl isobutyl ketone or diacetone alcohol, polyols, such as ethylene glycol, propylene glycol, butylene glycol, 1,4-butanediol, 1,5-pentanediol, 1,6-hexanediol, diethylene glycol, triethylene glycol, trimethylolpropane, polyethylene glycol or polypropylene glycol with a mean gram-molecular weight of 100 to 4000 g/mol or 200 to 1500 g/mol, or glycerol, monohydroxyethers, such as monohydroxyalkyl ethers or mono-$C_1$-$C_4$-alkyl glycol ethers such as ethylene glycol monoethyl ether, ethylene glycol monomethyl ether, diethylene glycol monomethyl ether or diethylene glycolmonoethyl ether, diethylene glycol monobutyl ether, dipropylene glycol monoethyl ether, thiodiglycol, triethylene glycol monomethyl ether or triethylene glycol monoethyl ether, furthermore 2-pyrrolidone, N-methyl-2-pyrrolidone, N-ethyl-pyrrolidone, N-vinylpyrrolidone, 1,3-dimethylimidazolidone, dimethylacetamide and dimethyl formamide.

The amount of the solvents employed in the aqueous continuous phase is in general less than 60% by weight or less than 40% by weight, based on the continuous phase.

Surface-active agents are understood as meaning emulsifiers, wetters, dispersants, antifoams or solubilizers which are soluble or fully soluble, in the aqueous phase. In particular, they can be nonionic, anionic, multicationic or amphoteric or of monomeric, oligomeric or polymeric nature. The choice of the surface-active agents is not limited in accordance with the present invention and must be matched with the discontinuous phase to be stabilized with regard to the desired type of emulsion (for example miniemulsion or mieroemulsion) and the stability of the emulsion, in particular the sedimentation and/or creaming of the disperse phase.

Examples of suitable surface-active agents include the following: a) alkoxylation product which can be obtained by ethylene-oxide-alkoxylation or propylene-oxide-alkoxylation of condensates of phenolic OH-containing aromatics with formaldehyde and NH functional groups; b) inorganic salts which are soluble in water, such as borates, carbonates, silicates, sulfates, sulfites, selenates, chlorides, fluorides, phosphates, nitrates and aluminates of the alkali metals and alkaline earth metals and other metals and also ammonium; c) polymers composed of recurrent succinyl units, in particular polyaspartic acid; d) nonionic or ionically modified compounds form the group of the alkoxylates, alkylolamides, esters, amine oxides and alkyl polyglycosides, including reaction products of alkylene oxides with compounds capable of being alkylated, such as, for example, fatty alcohols, fatty amines, fatty acids, phenols, alkyl phenols, carboximides and resinic acids. These are, for example, ethylene oxide adducts from a class of the reaction products of ethylene oxide with: 1) saturated and/or unsaturated fatty alcohols with 6 to 25 C atoms or 2) alkyl phenols with 4 to 12 C atoms in the alkyl radical or 3) saturated and/or unsaturated fatty amines with 14 to 20 C atoms or 4) saturated and/or unsaturated fatty acids with 14 to 22 C atoms or 5) hydrogenated and/or unhydrogenated resinic acids, or 6) esterification and/or arylation products prepared from natural or modified, optionally hydrogenated castor oil lipid bodies which, if appropriate, are linked by esterification with dicarboxylic acids to give recurrent structural units; e) ionic or nonionic compounds from the group of the reaction products of alkylene oxide with sorbitan ester, oxalkylated acetylene diols and acetylene glycols, and oxalkylated phenols; f) ionic or nonionic polymeric surface-active agents from the group of the homo- and copolymers, graft and graft copolymers and random and linear block copolymers. Examples of such suitable polymeric surface-active agents include polyethylene oxides, polypropylene oxides, polyoxymethylenes, polytrimethylene oxides, polyvinyl methyl ethers, polyethylene imines, polyacrylic acid, polyaryl amides, polymethacrylic acids, polymethacrylamides, poly-N,N-dimethyl-acrylamides, poly-N-isopropyl acrylamides, poly-N-acrylglycinamides, poly-N-methacrylglycinamides, polyvinyloxazolidones, polyvinylmethyloxazolidones; g) anionic surface-active agents such as, for example, alkyl sulfates, ether sulfates, ether carboxylates, phosphate esters, sulfosuccinate amides, paraffin sulfonates, olefin sulfonates, sarcosinates, isothionates and taurates; h) anionic surface-active agents from the group of what is known as dispersants, in particular condensates which can be obtained by reacting naphthols with alkanols, subjecting alkylene oxide to an addition reaction and at least partially converting the terminal hydroxyl groups into sulfo groups or monoesters of maleic acid, phthalic acid or succinic acid, sulfosuccinic esters, alkylbenzene sulfonates, and salts of the polyacrylic acids, polyethylene sulfonic acids, polystyrene sulfonic acid, polymethacrylic acids, polyphosphoric acids; i) lignin-type compounds, especially lignosulfonates, for example those which have been obtained by the sulfite or Kraft method. They include products which are partially hydrolyzed, oxidized, propoxylated, sulfonated, sulfomethylated or bisulfonated and which are fractionated by known methods, for example according to the molecular weight or the degree of sulfonation. Mixtures of sulfite and Kraft lignosulfonates are also very effective. Suitable are lignosulfonates with a mean molecular weight of greater than about 1,000 to 100,000, a content of active lignosulfonate of at least 80% and, a low content of polyvalent cations. The degree of sulfonation can be varied within wide limits.

In another embodiment, the continuous aqueous phase can also contain, in addition to the abovementioned surface-active agents, water-soluble block or block copolymers; these block or block copolymers include water-soluble block and block copolymers based on ethylene oxide and/or propylene oxide and/or water-soluble block and block copolymers of ethylene oxide and/or propylene oxide on bifunctional amines. Block copolymers based on polystyrene and polyalkylene oxide, poly(meth)acrylates and polyalkylene oxide and also poly(meth)acrylates and poly(meth)acrylic acids are also suitable.

In addition, the continuous aqueous phase can also contain further customary adjuvants such as, for example, water-soluble wetters, antifoams and/or preservatives.

Emulsion types of the present invention which may be mentioned are: macroemulsion: contains droplets>2 μm (microscopic); miniemulsion: droplet diameter 0.1 to 2 μm, turbid; and microemulsion: droplet diameter<0.1 μm; transparent. For additional examples of emulsions and hydrogels suitable for the present invention see U.S. Pat. Nos. 6,458,373 and 6,124,273.

(iv) Nanoparticles and Microparticles

Examples of nanoparticles and microparticles that can be used as a carrier in the present invention are include porous particles having a mass density less than 1.0 g/cm$^3$, or less than about 0.4 g/cm$^3$. The porous structure permits, for example, deep lung delivery of relatively large diameter therapeutic aerosols, for example greater than 5 μm in mean diameter.

The porous particles preferably are biodegradable and biocompatible, and optionally are capable of biodegrading at a controlled rate for delivery of a drug. The porous particles may be made of any material which is capable of forming a porous particle having a mass density less than about 0.4 g/cm$^3$. Both inorganic and organic materials can be used. For example, ceramics may be used. Other non-polymeric materials may be used which are capable of forming porous particles as defined herein.

The particles may be formed from any biocompatible, and preferably biodegradable polymer, copolymer, or blend, which is capable of forming porous particles having a density less than about 0.4 g/cm$^3$.

Surface eroding polymers such as polyanhydrides may be used to form the porous particles. For example, polyanhydrides such as poly[(p-carboxyphenoxy)-hexane anhydride] ("PCPH") may be used. Biodegradable polyanhydrides are described, for example, in U.S. Pat. No. 4,857,311.

In another embodiment, bulk eroding polymers such as those based on polyesters including poly(hydroxy acids) can be used. For example, polyglycolic acid ("PGA") or polylactic acid ("PLA") or copolymers thereof may be used to form the porous particles, wherein the polyester has incorporated therein a charged or functionalizable group such as an amino acid as described below.

Other polymers include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses, polysaccharides, and peptides or proteins, or copolymers or blends thereof which are capable of forming porous particles with a mass density less than about 0.4 g/cm$^3$. Polymers may be selected with or modified to have the appropriate stability and degradation rates in vivo for different controlled drug delivery applications.

As another example, the porous particles may be formed from functionalized polyester graft copolymers, as described in Hrkach et al., Macromolecules, 28:4736-4739 (1995); and Hrkach et al., "Poly(L-Lactic acid-co-amino acid) Graft Copolymers: A Class of Functional Biodegradable Biomaterials" in Hydrogel and Biodegradable Polymers for Bioapplications, ACS Symposium Series No. 627, Raphael M. Ottenbrite et al., Eds., American Chemical Society, Chapter 8, pp. 93-101, 1996, the disclosures of which are incorporated herein by reference. The functionalized graft copolymers are copolymers of polyesters, such as poly(glycolic acid) or poly(lactic acid), and another polymer including functionalizable or ionizable groups, such as a poly(amino acid). In another embodiment, comb-like graft copolymers are used which include a linear polyester backbone having amino acids incorporated therein, and poly(amino acid) side chains which extend from the amino acid groups in the polyester backbone. The polyesters may be polymers of α-hydroxy acids such as lactic acid, glycolic acid, hydroxybutyric acid and valeric acid, or derivatives or combinations thereof. The inclusion of ionizable side chains, such as polylysine, in the polymer has been found to enable the formation of more highly porous particles, using techniques for making microparticles known in the art, such as solvent evaporation. Other ionizable groups, such as amino or carboxyl groups, may be incorporated, covalently or non-covalently, into the polymer to enhance porosity. For example, polyaniline could be incorporated into the polymer.

An exemplary polyester graft copolymer, which may be used to form porous polymeric particles is the graft copolymer, poly(lactic acid-co-lysine-graft-lysine) ("PLAL-Lys"), which has a polyester backbone consisting of poly (L-lactic acid-co-Z-L-lysine) (PLAL), and grafted lysine chains. PLAL-Lys is a comb-like graft copolymer having a backbone composition, for example, of 98 mol % lactic acid and 2 mol % lysine and poly(lysine) side chains extending from the lysine sites of the backbone.

The use of the poly(lactic acid) copolymer is advantageous since it biodegrades into lactic acid and lysine, which can be processed by the body. The existing backbone lysine groups are used as initiating sites for the growth of poly (amino acid) side chains.

In the synthesis, the graft copolymers may be tailored to optimize different characteristic of the porous particle including: i) interactions between the agent to be delivered and the copolymer to provide stabilization of the agent and retention of activity upon delivery; ii) rate of polymer degradation and, thereby, rate of drug release profiles; iii) surface characteristics and targeting capabilities via chemical modification; and iv) particle porosity. For additional examples of nanoparticles and microparticles suitable for the present invention see U.S. Pat. Nos. 6,447,753 and 6,274,175.

(v) Solid Surface

In certain embodiments, the carrier used in the present invention may be a solid support, e.g., a polymer bead or a resin, e.g., a Wang resin. Supports can be solids having a degree of rigidity such as silicon, plastic, and the like. Support can also be flexible materials such as plastic or otherwise synthetic materials (such as nylon), materials made of natural polymers (such as cellulose or silk) or derivatives thereof (such as nitrocellulose) and the like. In certain embodiments the support is a porous material which can be rigid or flexible, intermeshed fibers including woven fabrics, and the like. In some embodiments, the solid support is a bead or pellet, which can be porous.

Another option for creating a solid support with reactive sites is to directly derivatize the solid support so that it can be coupled to a compound. The chemistry used to do this can be the same or similar to that used to derivatize controlled pore glass (cpg) beads and polymer beads. Typically, the first step in this process is to create hydroxyl groups (if they do not already exist on the support) or amino groups on the support. If hydroxyl groups exist or are created, they are typically converted to amino groups, for instance by reacting them with gamma-aminopropyl triethoxy silane. MBDs can be added to the amino groups with cyclic acid anhydrides, activated esters, reactions with polymerized alkylene oxides and other methods known to the art.

Another method to increase the reactive surface area of a solid support is to create columnar structures of silicon monoxide, for instance by thermal evaporation of SiO$_x$. Another such method is to insert into the reaction cells fabrics, such as non-woven glass or plastic (preferably fiberglass or polypropylene fiber) fabrics and plasma treating the fabric to create reactive sites. Still another method uses spin-on glass, which creates a thin film of nearly stoichiometric SiO$_2$ from a sil-sesquioxane ladder polymer structure by thermal oxidation. Sol-gel processing creates thin films of glass-like composition from organometallic starting materials by first forming a polymeric organometallic structure in mixed alcohol plus water and then careful drying and baking. When the sol-gel system is dried above the critical temperature and pressure of the solution, an aerogel results. Aerogels have chemical compositions that are similar to glasses (e.g. SiO$_2$) but have extremely porous microstructures. Their densities are comparably low, in some cases having only about one to about three percent solid composition, the balance being air.

In one embodiment, the carrier is a liposome comprising one or more lipids. The lipids used in the compositions of the present invention can be synthetic, semi-synthetic or naturally-occurring lipids, including phospholipids, tocopherols, steroids, fatty acids, glycoproteins such as albumin, anionic lipids and multicationic lipids. The lipids may be anionic, multicationic, or neutral. In one embodiment, the lipid formulation is substantially free of anionic lipids. In one embodiment, the lipid formulation comprises only neutral lipids. In another embodiment, the lipid formulation is free of anionic lipids. In another embodiment, the lipid is a phospholipid. Phospholipids include egg phosphatidylcholine (EPC), egg phosphatidylglycerol (EPG), egg phosphatidylinositol (EPI), egg phosphatidylserine (EPS), phosphatidylethanolamine (EPE), and egg phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The chains on these fatty acids can be saturated or unsaturated, and the phospholipid can be made up of fatty acids of different chain lengths and different degrees of unsaturation. In particular, the compositions of the formulations can include dipalmitoylphosphatidylcholine (DPPC), a major constituent of naturally-occurring lung surfactant as well as dioleoylphosphatidylcholine (DOPC). Other examples include dimyristoylphosphatidylcholine (DMPC) and dimyristoylphosphatidylglycerol (DMPG) dipalmitoylphosphatidcholine (DPPC) and dipalmitoylphosphatidylglycerol (DPPG) distearoylphosphatidylcholine (DSPC) and distearoylphosphatidylglycerol (DSPG), dioleylphosphatidylethanolamine (DOPE) and mixed phospholipids like palmitoylstearoylphosphatidylcholine (PSPC) and palmitoylstearoylphosphatidylglycerol (PSPC), driacylglycerol, diacylglycerol, seranide, sphingosine, sphingomyelin and single acylated phospholipids like mono-olcoyl-phosphatidylcthanol amine (MOPE).

The lipids used can include ammonium salts of fatty acids, phospholipids and glycerides, steroids, phosphatidylglycerols (PGs), phosphatidic acids (PAs), phosphotidylcholines (PCs), phosphatidylinositols (PIs) and the phosphatidylserines (PSs). The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9 (Z)-octadecenyloxy)-prop-1-yl-N,N,N-trimethylammonium chloride (DOTMA) and 1,2-bis(oleoyloxy)-3-(trimethylammonio)propane (DOTAP). Examples of steroids include cholesterol and ergosterol. Examples of PGs, PAs, PIs, PCs and PSs include DMPG, DPPG, DSPG, DMPA, DPPA, DSPA, DMPI, DPPI, DSPI, DMPS, DPPS and DSPS, DSPC, DPPG, DMPC, DOPC, egg PC.

Liposomal antibiotic formulations composed of phosphatidylcholines, such as DPPC, aid in the uptake by the cells in the lung such as the alveolar macrophages and helps to sustain release of the antiinfective agent in the lung (Gonzales-Rothi et al. (1991)). The negatively charged lipids such as the PGs, PAs, PSs and PIs, in addition to reducing particle aggregation, can play a role in the sustained release characteristics of the inhalation formulation as well as in the transport of the formulation across the lung (transcytosis) for systemic uptake. The sterol compounds are believed to affect the release and leakage characteristics of the formulation.

Liposomes are completely closed lipid bilayer membranes containing an entrapped aqueous volume. Liposomes can be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase. Lipid antiinfective formulations are associations lipid and the antiinfective agent. This association can be covalent, ionic, electrostatic, noncovalent, or steric. These complexes are non-liposomal and are incapable of entrapping additional water soluble solutes. Examples of such complexes include lipid complexes of amphotericin B (Janoff et al., Proc. Nat Acad. Sci., 85:6122 6126, 1988) and cardiolipin complexed with doxorubicin.

A lipid clathrate is a three-dimensional, cage-like structure employing one or more lipids wherein the structure entraps a bioactive agent. Such clathrates are included in the scope of the present invention.

Proliposomes are formulations that can become liposomes or lipid complexes upon corning in contact with an aqueous liquid. They can generally be in the form of a powder, paste, or film. Agitation or other mixing may be necessary. Such proliposomes are included in the scope of the present invention.

The process for forming lipid drug formulations involves a "solvent infusion" process. This is a process that includes dissolving one or more lipids in a small, preferably minimal, amount of a process compatible solvent to form a lipid suspension or solution (preferably a solution) and then infusing the solution with an aqueous medium containing the drug. Typically a process compatible solvent is one that can be washed away in a aqueous process such as dialysis or diafiltration. "Ethanol infusion," a type of solvent infusion, is a process that includes dissolving one or more lipids in a small, preferably minimal, amount of ethanol to form a lipid solution and then infusing the solution with an aqueous medium containing the drug. A "small" amount of solvent is an amount compatible with forming liposomes or lipid complexes in the infusion process. It is key that the conditions for the infusion process have to lead to coacervate formation. Ultimate conditions for infusing a given lipid solution with a given aqueous solution of the active agent have to be determined based on the Examples presented herein and the effect of various parameters taught below. Also useful to someone of ordinary skill in the art, are the techniques for forming coacervates as described in such references as Bunderberg de Jong, H. G., Kruyt, H. R. Koazevation (Entmischung in Kolloidalen Systemen), Koll. Zeitsch. 1930, 50(10), 39-48; Gander B, Blanco-Prieto M. J., Thomasin C, Wandrey Ch. and Hunkeler D., Coacervation/Phase Separation. In: Encyclopedia of Pharmaceutical Technology, Vol. 1, Swarbrick J, Boylan J. C., Eds., Marcel Dekker, 2002, p. 481-497; Newton D. W. Coacervation: Principles and Applications. In: Polymers for Controlled drug delivery. Tarcha P. J., Ed., CRC Press, Boca Raton, 1991, 67-81; Scott P. W., Williams A. C., Barry B. W., Characterization of complex coacervates of Some Tricyclic Antidepressants and evaluation of their potential for Enhancing Transdermal Flux. J. Controlled Release 1996, 41 (3), 215-227; Thomasin C., Merkle H. P., Gander B. Drug microencapsulation by PLA/PLGA Coacervation in the Light of Thermodynamics. 2. Parameters determining Microsphere Formation. J. Pharm Sci. 1998, 87 (30), 269-275; Ball V., Winterhalter M., Schwinte P., Lavalle Ph., Voegel J.-C., Schaal P. Complexation mechanism of Bovine Serum Albumin and Poly(allylamine hydrochloride). J. Phys. Chem. B. 2002, 106, 2357-2364; Mohanty B., Bohidar H. B. Systematic of Alcohol-Induced Simple Coacervation in Aqueous Gelatin Solutions. Biomacromolecules 2003, 4, 1080-1086, all of which are incorporated herein by reference in their entirety. Preferably, the step is performed by an in-line infusion process.

Liposome or lipid formulation sizing can be accomplished by a number of methods, such as extrusion, sonication and homogenization techniques which are well known, and readily practiced, by ordinarily skilled artisans. Extrusion involves passing liposomes, under pressure, one or more times through filters having defined pore sizes. The filters are generally made of polycarbonate, but the filters may be made of any durable material which does not interact with the liposomes and which is sufficiently strong to allow extrusion under sufficient pressure. Preferred filters include "straight through" filters because they generally can withstand the higher pressure of the preferred extrusion processes of the present invention. "Tortuous path" filters may also be used. Extrusion can also use asymmetric filters, such as Anopore™ filters, which involves extruding liposomes through a branched-pore type aluminum oxide porous filter.

Liposomes or lipid formulations can also be size reduced by sonication, which employs sonic energy to disrupt or shear liposomes, which will spontaneously reform into smaller liposomes. Sonication is conducted by immersing a glass tube containing the liposome suspension into the sonic epicenter produced in a bath-type sonicator. Alternatively, a probe type sonicator may be used in which the sonic energy is generated by vibration of a titanium probe in direct contact with the liposome suspension. Homogenization and milling apparatii, such as the Gifford Wood homogenizer, Polytori™ or Microfluidizer, can also be used to break down larger liposomes or lipid formulations into smaller liposomes or lipid formulations.

The resulting liposomal formulations can be separated into homogeneous populations using methods well known in the art; such as tangential flow filtration. In this procedure, a heterogeneously sized population of liposomes or lipid formulations is passed through tangential flow filters, thereby resulting in a liposome population with an upper and/or lower size limit. When two filters of differing sizes, that is, having different pore diameters, are employed, liposomes smaller than the first pore diameter pass through the filter. This filtrate can the be subject to tangential flow filtration through a second filter, having a smaller pore size than the first filter. The retentate of this filter is a liposomal/complexed population having upper and lower size limits defined by the pore sizes of the first and second filters, respectively.

Mayer et al. found that the problems associated with efficient entrapment of lipophilic ionizable bioactive agents such as antineoplastic agents, for example, anthracyclines or vinca alkaloids, can be alleviated by employing transmembrane ion gradients. Aside from inducing greater uptake, such transmembrane gradients can also act to increase drug retention in the liposomal formulation.

Lipid drug formulations have a sustained effect and lower toxicity allowing less frequent administration and an enhanced therapeutic index. In preclinical animal studies and in comparison to inhaled tobramycin (not-liposomal or lipid-based) at the equivalent dose level, liposomal amikacin was shown to have, during the time period shortly after administration to over 24 hours later, drug levels in the lung that ranged from two to several hundred times that of tobramycin. Additionally, liposomal amikacin maintained these levels for well over 24 hours. In an animal model designed to mimic the *pseudomonas* infection seen in CF patients, liposomal amikacin was shown to significantly eliminate the infection in the animals' lungs when compared to free aminoglycosides.

Lung surfactant allows for the expansion and compression of the lungs during breathing. This is accomplished by coating the lung with a combination of lipid and protein. The lipid is presented as a monolayer with the hydrophobic chains directed outward. The lipid represents 80% of the lung surfactant, the majority of the lipid being phosphatidylcholine, 50% of which is dipalmitoyl phosphatidylcholine (DPPC) (Veldhuizen et al, 1998). The surfactant proteins (SP) that are present function to maintain structure and facilitate both expansion and compression of the lung surfactant as occurs during breathing. Of these, SP-B and SP-C specifically have lytic behavior and can lyse liposomes (Hagwood et al., 1998; Johansson, 1998). This lytic behavior could facilitate the gradual break-up of liposomes. Liposomes can also be directly ingested by macrophages through phagocytosis (Couveur et al., 1991; Gonzales-Roth et al., 1991; Swenson et al, 1991). Uptake of liposomes by alveolar macrophages is another means by which drugs can be delivered to the diseased site.

The lipids preferably used to form either liposomal or lipid formulations for inhalation are common to the endogenous lipids found in the lung surfactant. Liposomes are composed of bilayers that entrap the desired drug. These can be configured as multilamellar vesicles of concentric bilayers with the drug trapped within either the lipid of the different layers or the aqueous space between the layers. The present invention utilizes unique processes to create unique liposomal or lipid drug formulations. Both the processes and the product of these processes are part of the present invention.

In one particularly preferred embodiment, the lipid drug formulations of the present invention are prepared by an in-line infusion method where a stream of lipid solution is mixed with a stream of drug solution in-line. For example, the two solutions may be mixed in-line inside a mixing tube preceded by a Y or T-connector. In this way, the in-line infusion method creates the best conditions for forming a drug coacervate. This infusion method results in lower lipid to drug ratios and higher encapsulation efficiencies and is described in U.S. patent application Ser. No. 11/185,448, incorporated herein in its entirety.

In another particularly preferred embodiment, the lipid drug formulations of the present invention are prepared by vortexing a lipid-organic solvent solution with an aqueous drug solution at a suitable vortexing level.

Another novel method of preparing the lipid drug formulations of the present invention involves initially encapsulating the multicationic drug by way of forming a coacervate with the multicationic drug in the presence of a lipid. It is believed that this technique will lead to low lipid to cation drug ratios and is described in U.S. patent application Ser. No. 11/398,859, which is incorporated herein in its entirety.

Remote Loading, where drug is introduced into the interior of the lipid formulation via ion exchange across the lipid membrane between the charged drug and positive ions of the anionic counter ions, is another way in which compositions of the present invention may be prepared. Examples of remote loading are disclosed in U.S. Pat. Nos. 5,316,771 and 5,192,549, both of which are incorporated herein by reference in their entirety.

VII. Compositions

In its broadest embodiment, the compositions of the present invention comprise a multicationic drug and an organic multianion. The multicationic drug may be completely enclosed within a carrier such as a liposome or it may only be partially enclosed, that is, some of the multicationic drug may exist outside the carrier in an aqueous carrier, for example. The compositions of the present invention may also comprise encapsulated multicationic drug and encapsulated organic multianion. In another embodiment, at least some of the organic multianion is non-encapsulated. In this embodiment, the organic multianion may exist in an aqueous carrier, for example, or it may coordinate to the outer surface of the liposome through electrostatic forces. Importantly, the organic multianion is in close proximity of the multicationic drug. For example, upon release of the multicationic drug from the interior of the liposome, the organic multianion will be close enough to form a multicationic drug-counter ion complex. One of ordinary skill in the art is aware that the organic multianions exist in equilibrium with their protonated acid form.

VIII. Efficacy of Treatment

The efficacy of treatment with the subject compositions may be determined in a number of fashions known to those of skill in the art.

In one exemplary method, the median survival rate of the microbe or microbial median survival time or life span for treatment with a subject composition may be compared to other forms of treatment with the particular compound of the present invention or multicationic drug contained in the subject composition, or with other multicationic drugs. The decrease in median microbial survival rate or time or life span for treatment with a subject composition as compared to treatment with another method may be 10, 25, 50, 75, 100, 150, 200, 300, 400% less or even more. The period of time for observing any such decrease may be about 3, 5, 10, 15, 390, 60 or 90 or more days. The comparison may be made against treatment with the multicationic drug contained in the subject composition, or with other drugs, or administration of the same or different drugs by a different method, or administration as part of a different drug delivery device than a subject composition. The comparison may be made against the same or a different effective dosage of the various drugs. The different regiments compared may use microbial levels.

Alternatively, a comparison of the different treatment regimens described above may be based on the effectiveness of the treatment, using standard indicies for microbial infections known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different composition of the present invention.

IX. Dosages

The dosage of any compositions of the present invention will vary depending on the symptoms, age and body weight of the patient, the nature and severity of the pulmonary distress to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., an aminoglycoside) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

The compositions of the present invention may be in a single dosage form or in a multiple dosage form. For example, it is envisioned by the inventors that when the composition comprises an aminoglycoside and another type of antiinfective that the aminoglycoside and antiinfective may be in a single dosage form or in separate dosage forms. In the latter example the separate dosage forms would still be considered a composition of the present invention. It is also envisioned by the inventors that when the compositions of the present invention are in multiple dosage forms, the dosage forms may be administered to a subject concurrently or sequentially. When the dosage forms are administered sequentially, conceivably any time period may apply between dosages. Generally the time period applied will be in accordance with a physicians directions. In one embodiment, the time period between dosages may be 30 seconds, 1 minute, 5 minutes, 1 hour, 2 hours, or more.

In another embodiment, the dosage forms may be administered to a subject in treatment cycles. For instance a subject may be treated with a composition of the present invention any where from a single dosage to several dosages over the course of a day, or repeat this regiment for any amount of days followed by a break in the regiment for any number of days, weeks, or months before starting the cycle again. For example, a subject may receive treatment with a composition of the present invention daily from anywhere from 1 to 7 days followed by a period of non-treatment from anywhere from 0 to 7 days. A subject may therefore receive treatment daily, once every 2 days, once every 3 days, once a week, once every two weeks, once a month . . . etc. to name just a few non-limiting examples.

X. Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A composition comprising a multicationic aminoglycoside enclosed within a liposome and an organic multianion outside the liposome in close proximity to the aminoglycoside to allow for the formation of an aminoglycoside-counter ion complex upon release of the aminoglycoside from the interior of the liposome, wherein the organic multianion is selected from the group consisting of citrate, maleate, tartarate, glutarate, succinate, malonate, adipate, pimelate, suberate, azelate, sebacate, and terephthalate, the concentration of anionic groups of the organic multianion is at least 30 mM, and the organic multianion reduces binding of the aminoglycoside to a polyanionic biofilm associated with a pulmonary disease, and an inhalation device.

2. The composition of claim 1, further comprising an organic multianion that is enclosed within the liposome.

3. The composition of claim 1, wherein the multicationic aminoglycoside is selected from the group consisting of amikacin, gentamicin, kanamycin, neomycin, netilmicin, paromomycin, streptomycin, tobramycin, and aparmycin.

4. The composition of claim 1, wherein the multicationic aminoglycoside is amikacin and the organic multianion is citrate.

5. The composition of claim 1, wherein the liposome comprises a phospholipid.

6. The composition of claim 1, wherein the liposome comprises a sterol.

7. The composition of claim 1, wherein the liposome comprises a lipid selected from the group consisting of egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleylphosphatidyl-ethanolamine (DOPE), palmitoylstearoylphosphatidyl-choline (PSPC), palmitoylstearolphosphatidylglycerol (PSPG), mono-oleoyl-phosphatidylethanolamine (MOPE), cholesterol, ergosterol, lanosterol, tocopherol, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2 3-di-(9-(Z)-octadecenyloxy)-prop-1-yl-N,N,N-trimethylammonium chloride (DOTMA), 1,2-bis(oleoyloxy)-3-(trimethylammonio)propane (DOTAP), phosphatidyl-glycerols (PGs), phosphatidic acids (PAs), phosphatidylinositols (PIs), phosphatidyl serines (PSs), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphosphatidylinositol (DSPI), dimyristoylphosphatidylserine (DMPS), dipalmitoylphosphatidylserine (DPPS), distearoylphosphatidylserine (DSPS), and mixture thereof.

8. The composition of claim 1, wherein the liposome comprises a phospholipid and a sterol.

9. The composition of claim 1, wherein the liposome comprises DPPC and cholesterol.

10. The composition of claim 1, wherein the multicationic aminoglycoside is amikacin, the organic multianion is citrate, and the liposome comprises DPPC and cholesterol.

11. The composition of claim 1, in the form of a liquid.

12. The composition of claim 11, wherein the liquid is an aqueous solution.

13. The composition of claim 1, wherein the concentration of anionic groups of the organic multianion is at least 100 mM.

14. A method of ameliorating at least one symptom of pulmonary distress in a subject in need thereof, comprising administering to the subject via an inhalation device an effective amount of a composition comprising a multicationic aminoglycoside enclosed within a liposome and an organic multianion outside the liposome in close proximity to the aminoglycoside to allow for the formation of an aminoglycoside-counter ion complex upon release of the aminoglycoside from the interior of the liposome, wherein the organic multianion is selected from the group consisting of citrate, maleate, tartarate, glutarate, succinate, malonate, adipate, pimelate, suberate, azelate, sebacate, and terephthalate, the concentration of anionic groups of the organic multianion is at least 30 mM, and the organic multianion reduces binding of the multicationic aminoglycoside to a polyanionic biofilm associated with a pulmonary disease.

15. The method of claim 14, wherein the pulmonary distress is cystic fibrosis or pneumonia.

16. The method of claim 14, wherein the pulmonary distress is cystic fibrosis.

17. The method of claim 14, wherein the subject is a mammal.

18. The method of claim 14, wherein the subject is a human, primate, equine, bovine, porcine, canine, feline, or rodent.

19. The method of claim 14, wherein the subject is a human.

20. The composition of claim 1, wherein the polyanionic biofilm comprises alginate.

* * * * *